(12) United States Patent
Kates et al.

(10) Patent No.: US 7,801,839 B2
(45) Date of Patent: Sep. 21, 2010

(54) METHOD FOR TRAINING A LEARNING-CAPABLE SYSTEM

(76) Inventors: Ronald E. Kates, Palnkamer Strasse 49, Otterfing (DE) 83624; Nadia Harbeck, Palnkamer Strasse 49, Otterfing (DE) 83624

( * ) Notice: Subject to any disclaimer, the term of this patent is extended or adjusted under 35 U.S.C. 154(b) by 757 days.

(21) Appl. No.: 10/520,409

(22) PCT Filed: Jul. 3, 2003

(86) PCT No.: PCT/EP03/07112

§ 371 (c)(1),
(2), (4) Date: Jul. 22, 2006

(87) PCT Pub. No.: WO2004/006041

PCT Pub. Date: Jan. 15, 2004

(65) Prior Publication Data

US 2006/0248031 A1    Nov. 2, 2006

(30) Foreign Application Priority Data

Jul. 4, 2002   (EP) .................................. 02014857

(51) Int. Cl.
*G06F 15/18*   (2006.01)
(52) U.S. Cl. .............................. 706/21; 706/12; 706/15; 706/16; 706/17; 706/18; 706/19; 706/20
(58) Field of Classification Search ............ 706/12, 706/15–21, 25, 924; 600/300, 301, 408
See application file for complete search history.

(56) References Cited

U.S. PATENT DOCUMENTS

| | | | | |
|---|---|---|---|---|
| 5,577,166 A | * | 11/1996 | Mizuno | .................... 706/20 |
| 5,703,964 A | * | 12/1997 | Menon et al. | ................ 382/228 |
| 6,059,724 A | * | 5/2000 | Campell et al. | ............. 600/300 |
| 6,248,063 B1 | * | 6/2001 | Barnhill et al. | ............. 600/300 |
| 6,282,529 B1 | | 8/2001 | Neuneier et al. | |
| 6,306,087 B1 | * | 10/2001 | Barnhill et al. | ............. 600/300 |
| 6,571,227 B1 | * | 5/2003 | Agrafiotis et al. | ............. 706/15 |
| 6,789,069 B1 | * | 9/2004 | Barnhill et al. | ............... 706/12 |
| 6,882,990 B1 | * | 4/2005 | Barnhill et al. | ............... 706/16 |

(Continued)

FOREIGN PATENT DOCUMENTS

EP   0528399 A2   2/1993

(Continued)

OTHER PUBLICATIONS

Cho et al., "Evolution of Neural Network Training Set through Addition of Virtual Samples." Prcdngs of IEEE Intnl. Conference on Evolutionary Computation, May 20, 1996, pp. 685-688.

*Primary Examiner*—Donald Sparks
*Assistant Examiner*—Omar F Fernandez Rivas
(74) *Attorney, Agent, or Firm*—IP Strategies

(57) ABSTRACT

The invention is directed to a method for training at least one learning-capable system comprising the steps of providing a predetermined training data set corresponding to a predetermined number of subjects comprising a predetermined input data set and a predetermined outcome data set, augmenting the input data set and/or the outcome data set, and training each learning-capable system using the augmented input data set and/or the augmented outcome data set.

19 Claims, 9 Drawing Sheets

U.S. PATENT DOCUMENTS

| | | | |
|---|---|---|---|
| 6,917,926 B2 * | 7/2005 | Chen et al. | 706/12 |
| 7,058,617 B1 * | 6/2006 | Hartman et al. | 706/16 |
| 7,107,253 B1 * | 9/2006 | Sumner et al. | 706/45 |
| 2004/0073096 A1 * | 4/2004 | Kates et al. | 600/300 |
| 2008/0120267 A1 * | 5/2008 | Chen et al. | 706/61 |

FOREIGN PATENT DOCUMENTS

| | | |
|---|---|---|
| WO | WO-9810352 A1 | 3/1998 |
| WO | WO-9901825 A1 | 1/1999 |

\* cited by examiner

METHOD FOR TRAINING A LEARNING-CAPABLE SYSTEM

FIELD OF THE INVENTION

The invention is directed to a method for training a learning-capable system.

In particular, the invention relates to the fields of prognosis, risk assessment, intervention/treatment selection, and treatment outcome prediction for a subject who is a member of some category of subjects. It further relates to the field of outcomes research. The category of subjects could comprise patients with a disease such as primary breast cancer or a condition such as pregnancy for which evidence relating objectifiable and/or standardized explanatory subject characteristics (e.g., risk factors, population characteristics, real or proposed treatments) to outcomes (e.g., recovery, complications, relapse, death) is available, for example in the form of one or more published clinical studies, or from original data—even data with certain deficiencies often encountered in practice, such as missing data or non-randomness. The present invention provides a method for synthesizing independent sources of said evidence and performing certain adjustments on deficient or non-random data in order to yield automated and objective estimates of outcome probabilities or information supporting such an estimate for a subject, taking into account said subject's recorded individual explanatory characteristics and/or effects of population characteristics that the evidence may provide. The invention has applications in the areas of meta-analysis, evidence-based medicine, epidemiology, clinical trial design, intervention analysis, and decision support.

DEFINITIONS

The following definitions are used in what follows:

"Learning-capable system" is defined as an objectifiable procedure such as a neural network or recursive partitioning that is capable of inferring (or estimating) and representing a possibly nonlinear relationship between variable characteristics and outcomes from suitable training data presented to said system.

"Available" data means that the data is known, for example, from observations. This contrasts with "missing" data.

"Training data" are defined as an array of information containing one set of objective quantities per subject, such that the objective quantities include both the explanatory characteristics (input data) and the outcome information, which may be censored. "Censoring" is well known in survival analysis and refers to the fact that the observation time of a subject in a study may end before an endpoint occurs.

The "training" of a neural network is defined as a procedure resulting in specified values of all connections of a neural network (including weights, operating points, and other required parameters) of the prescribed architecture, such that given the explanatory factors required by the neural network, one or more scores or classification categories characterizing the outcome of interest for a new subject are determined. A trained neural network represents a specified relationship (e.g., a conditional probability distribution) relating explanatory factors to outcome. Analogously, "training" of a learning-capable system of another form is defined as a procedure resulting in specified values of all required parameters, such that, given the explanatory factors required by the system, one or more scores or classification categories characterizing the outcome of interest for a new subject are determined. The term "neural network bias" frequently used in scientific and technical neural network literature (which enters the formula for the output of a neuron) will be replaced here by the term "operating point" in order to distinguish it from the statistical concept of "bias" (e.g., "selection bias") as used repeatedly here, i.e., "bias" refers to statistical bias unless otherwise stated.

An "output" of a learning-capable system is defined as a quantity such as a score or a classification category which, when inserted into a specified representation, produces either desired information about the outcome or directly supports a decision (e.g., buy/sell, treat/observe, accept/reject). The process of obtaining said scores or classification categories from the output of a trained neural network or other learning-capable system is much simpler than the process of training, and it can be implemented for the purposes of the invention by a computer program, given the parameters and specifications of said trained system. The function of such a program is illustrated below. If a learning-capable system comprises several stages, such as a multi-layer neural network, the response or output of the internal stages or layers, e.g. the response of a hidden neuron in the case of a neural network, is called "internal output".

"Evidence" refers both to data available for each individual subject in a sample of subjects and information originally obtained from a sample of subjects but available only in aggregated form.

BACKGROUND OF THE INVENTION

Risk and Benefit Assessment

The assessment and estimation of outcome probabilities based on explanatory factors and proposed interventions or treatments plays a central role in medicine, engineering, public policy, business, finance, and insurance, etc. In a broad sense, the goal is to improve derivation of inferences about new situations from existing evidence.

The potential benefits of even a small improvement in risk and benefit assessment from evidence are substantial and far-reaching: In primary breast cancer, for example, an improvement in prognosis, i.e., probability distribution of distant metastasis-free survival or overall survival, could allow the oncologist and the patient to reach better adjuvant treatment decisions and thus lengthen patient survival. In engineering, improved prediction of time to failure of complex systems could allow better targeting of preventative interventions and thus optimize use of resources. In public policy, a typical application would be to predict which unemployed workers are most likely to benefit from "interventions" such as educational programs, or which persons should be targeted with measures to avoid recidivism in criminal justice cases, thus optimizing resources and utilizing human capital better. In business, expensive measures to avoid cancellations can be targeted to those most susceptible to cancellation. In finance, investors are interested in the probability that a stock price will severely drop (or will rise sharply) and can buy or sell accordingly; banks provide credit to customers on the basis of default assessment.

Assessment of benefits and risks often requires characterization of possibly complex relationships between subject characteristics (individual explanatory factors, proposed treatments, and population characteristics) and outcomes. Neural networks and other learning-based systems are tools that have been applied to modelling of complex relationships. However, the data required to train these tools is not always available in sufficient quantity and scope as original data from carefully controlled, randomized experimental studies. That is, original data may be lacking, or such original data that is available may have certain deficiencies that could affect the training of a learning-capable system. Issues addressed by the present invention include the question of how to improve the utilization of such evidence which may be available for the desired risk assessment.

Evidence Disaggregation and Synthesis

In many areas of medicine, an enormous body of scientifically verified clinical studies of medical conditions and diseases is potentially available to improve assessment of patient outcomes. For many conditions and diseases, databases listing published sources of evidence and classifying said sources according to various criteria may be readily obtained from generally accepted authorities (see for example http://www.cochrane.org).

However, in order for databases to aid in clinical practice, there is a need to estimate outcome probabilities for "new" subjects based on an objective and efficient application of the evidence. Such a need arises in principle in many fields outside of medicine as well. The quality or performance of such an estimation procedure depends on the method applied to derive assessments from the evidence. Currently available procedures for deriving such assessments have several severe deficits that are addressed by the present invention, as explained in what follows:

Limitations of Current Evidence-Based Approaches

It is generally true both of studies and of new subjects that not all characteristics of subjects that could affect outcome are recorded or even available for measurement. If, as is often the case, different characteristics are recorded in different studies, an explanatory factor X seen as "independent" or "relevant" for the outcome model in Study B can fail to be identified as relevant to the same outcome in Study A—even if X was measured in both A and B—for example because a second factor available in Study A was not measured in Study B. Even if exactly the same set of explanatory characteristics {X1, X2, . . . } are measured in two different studies, it is possible in the presence of multi-factorial (and sometimes multi-collinear) influences on outcome—due to statistical fluctuations or due to underlying differences in populations across studies—for different studies to indicate different subsets of explanatory characteristics deemed "relevant"; e.g., a staging factor deemed "redundant" in Study A may be identified as "relevant" in the statistical model of Study B. Even if the same factors are included as relevant in the models of A and B, the weights of parameters (e.g., regression coefficients) will always differ, sometimes substantially, especially if there is multi-collinearity.

Moreover, among the measurable set of explanatory characteristics of subjects within a category that could significantly affect outcome in principle, a subset (e.g., demographic variables or standards of care in a geographic region) tend to be constant within a given study, varying only across studies. This circumstance often occurs by design, with the intention of reducing unwanted heterogeneity. A population difference in outcome can indeed occur of course due for example to systematic differences in the distributions of explanatory (e.g., staging) factors, but a statistical model can control for such differences. However, even controlling for such differences in distributions of staging factors two studies may yield different outcome probability distributions. Due for example to unmeasured characteristics varying systematically across studies, two subjects from Study A and B, respectively, with seemingly identical staging factors (i.e., characteristics varying within the studies) could have different outcome probability distributions.

Different studies are performed with different numbers of subjects. Hence, even among a collection of high-quality studies on the same disease or condition, there could be some with a higher statistical power. These studies would be more likely for example to detect a significant influence of rarely occurring but important factors. Hence, one can imagine a new subject belonging to a population resembling that population sampled in some Study A, but with a rare staging factor whose significant impact was established in a (high powered) Study B. For this subject, it would be desirable to synthesize the evidence on special population characteristics of Study A with the evidence about the rare staging factor of Study B.

At present, the usual way to synthesize multiple sources of evidence is simply to rely on subjective judgements of experts (in medicine, physicians) who are presumed to know the evidence. However, subjective judgements, even those of experts, are generally acknowledged as the lowest level of evidence according to all established rating scales in evidence-based medicine. The quality of subjective judgements may vary in quality even among experts according to anecdotal experience, familiarity with scientific literature, as well as analytical synthesis capabilities, and neither the variation of quality from one practitioner to another, nor the degradation over time of even an expert synthesis, are predictable in any objective way from the evidence alone.

Improved objectivity in applying evidence to new subjects has sometimes been achieved by picking one "best" study (according to some subjective criteria) that includes some "standard" set of characteristics or factors and assuming that it applies to any new subject, even one who is more correctly described as belonging to a population used in a different study. However, according to this method, factors known for this new subject but not included in the model of the "best" study would simply be ignored, even if information on their impact were available from another study. In an ideal world, for any new subject belonging to a population A, a suitable study conducted in said population A and providing the risk of each outcome as a function of the recorded individual explanatory factors could always be found, as in a puzzle with all the pieces present and fitting together properly. In the real world, some of the puzzle pieces overlap, and others are missing. The evidence ("puzzle pieces") also have non-uniform quality (e.g., statistical power). Hence, if an assignment of patients to "nearest appropriate" studies were to be attempted, the following problems (among others) would in particular still arise 1. There may be no study for the outcome with a comparable population or with the factors required for assessing a new subject.
2. There may be two or more such studies that need not be perfectly concordant
3. Different studies have different statistical power; higher power is required for rare factors, but these factors may not have been measured in the "nearest" study.

The question thus arises of how to combine or synthesize the information in multiple sources of evidence more efficiently.

Published evidence is nearly always presented in an aggregated form; that is, the original data of each individual patient is rarely publicly available—often as a matter of policy—and there are important ethical reasons for such policies. The results of a study may for example provide a set of "IF-THEN" rules for outcomes or for decision support, but they may provide a statistical model relating subject explanatory characteristics to outcome probabilities in some form, such as a logistic or ordinary regression, a Cox proportional hazards model for survival, a classification and regression tree model, or another model well known to statisticians. Information on the (possibly multivariate) distribution of explanatory characteristics for the study may also be reported, such as the percentage of subjects in various subcategories (e.g., in the case of breast cancer, the percentages of patients having 0, 1, 2, . . . affected lymph nodes, or the correlation between tumor size and number of affected nodes). Often, published guidelines in medicine attempt to reduce the information contained in such detailed statistical models to a few IF-THEN decisions so that they can be applied by clinicians. This kind of reduction does not necessarily represent the best way of utilizing the evidence for an individual patient.

Scientific studies in fields such as medicine are expensive to perform, and the expense is closely related to the number of subjects required to achieve the required statistical power, which in turn is related to the size of the influence to be measured. In designing for example a randomized clinical study of a new treatment, a method for estimating outcome scores or classifications to potential subjects based on evidence could improve study efficiency by favoring selection of subjects whose outcomes are most likely to be influenced by the treatment in question. For example, accurate prediction of poor prognosis would greatly impact clinical trials for new breast cancer therapies, because potential study patients could then be stratified according to prognosis.

Trials of new therapy concepts could then be designed to focus on patients having poor prognosis in the absence of these new therapies, in turn making it easier to discern if said experimental therapy is efficacious.

Incorporation of Prior Evidence, Synthesis of Aggregated and Individual Data

Improved methods for permitting incorporation of prior evidence into advanced statistical models of "new" data would also be beneficial and are addressed by the invention. In a clinical setting, for example, current standards or practice may render it unethical to include an "untreated" control group in a new study measuring performance of a treatment, although such untreated control groups were considered ethical at a previous stage of medical knowledge. Hence, aggregated "evidence" may often provide the only available information allowing inferences about the new treatment compared to a hypothetical "untreated" group.

Independent Performance Measures

As a further issue addressed by the invention, independent performance measures are of great utility both in evaluating the evidence-based risk assessment environment and in further optimizing performance. The invention addresses this issue by providing an independent performance measures. This is accomplished by comparing predictions from the evidence synthesis tool with independent information, such as that of a study not originally incorporated into the tool.

Application to Other Fields

Although evidence-based approaches to decision support have received more attention in the medical context than elsewhere up to now, the present invention also is intended to address applications in any field in which trials relating objectifiable and/or standardized explanatory subject characteristics to outcomes may be available in aggregated form for various populations of subjects.

Outcomes Research and Observational Data

Even if individual data is available relating subject characteristics to outcomes, the data may not be ideal for a learning-capable system trained according to the state of the art to achieve the desired generalization performance. The desired generalization property includes not only system performance in predicting outcomes on a new sample drawn from a comparable population with the same treatment policy, but also the performance on a new sample drawn from a comparable population, conditional on treatment policy. This requirement arises for example if the goal is outcome estimation in a situation with treatment policies differing from those of the training set if the goal is optimization of treatments among several alternative or proposed strategies.

For many of the problems mentioned above, insufficient evidence from carefully conducted, randomized trials is available for training a learning-capable system, but there may be considerable retrospective or observational evidence (defined as data recorded from the observation of systems as they operate in normal practice). In the case of retrospective follow-up data in primary breast cancer, for example, the decision for administration of adjuvant systemic endocrine therapy or chemotherapy reflects guidelines and policies that have evolved over time and also can depend systematically on the study population. Moreover, outside of randomized trials, the probability of receiving a given treatment usually depends on explanatory factors in a manner that can vary from one study to another. Such dependencies are examples of "confounders," and they falsify or "bias" inferences on treatment efficacy. For example, in breast cancer, patients with many affected lymph nodes have usually been those most likely to receive chemotherapy, and hence a univariate comparison of relapse-free survival between patients receiving and not receiving chemotherapy would often find that chemotherapy is associated with poorer survival, the reason being in this case that selection bias is stronger than the benefit of therapy. The effect on outcome of differing population characteristics of groups selected for different treatments will be referred to in what follows as "selection bias".

Even "randomized" clinical studies often face the problem that subjects do not always adhere to protocols, e.g., some patients randomized to the control group will choose therapy and vice versa. Hence, a simple comparison of "treated" and "untreated" groups is not necessarily free of selection bias even in "randomized" clinical studies. For this reason a method of analyzing data known as "intention-to-treat" analysis has been advocated (see for example http://www-.consort-statement.org) and is often performed, in which all subjects are included in the group to which they were assigned, whether or not they completed the intervention (treatment) given to the group. Intention-to-treat analysis is randomized by definition, but it suffers from the deficiency that the true effects of treatment could be diluted by admixtures of the untreated subjects among the group that was intended to be treated and vice versa.

Observational data are often relatively plentiful and/or inexpensive to obtain, and they may be more representative of outcomes in an ordinary clinical setting than randomized trials. In fields outside of medicine, especially in social work, public policy, business, and finance, one often has no other alternative but to use data collected through the observation of systems as they operate in normal practice. Even in medicine, ethical requirements often restrict the range of permissible options for control groups.

Methods of outcomes research have been developed for assessing effectiveness of treatments from observational data. These methods of the current art generally provide a measure of the average effectiveness within a group of subjects, but they are limited in that they are not designed to provide an individualized estimate of therapy efficacy, i.e., an estimate that depends systematically on the explanatory characteristics of an individual subject. Moreover, the methods available up to now do not address the need to model complex impacts of explanatory factors and treatments on outcomes, including interactions of explanatory factors among themselves and with treatments (in clinical practice the latter interactions include "predictive impacts" of factors).

Learning-capable systems such as neural networks are appropriate for risk assessment in complex situations because they are able to detect and represent complex relationships between explanatory factors and outcomes even if the form of these complex relationships is unrestricted or not known a priori. This ability distinguishes them from conventional approaches, which are capable of detecting and representing only that subclass of relationships that satisfy the assumptions of the model, such as linear dependence.

Consider now the relationship between proposed interventions (e.g., therapies for a disease) and outcome probabilities for an individual subject. Of particular interest is the detection of explanatory factors or relationships that may be predictive of response to therapy for an individual patient. This is an inherently nonlinear and possibly complex problem for which learning-capable systems would seem to offer an appropriate approach. Unfortunately, when observational data are used to train such a system according to the state of the art, the treatment policy in the training set can affect the relationship between explanatory factors and outcomes so as to reduce the generalizability in the sense defined above. This deficiency of the state of the art applies to any relationship between treatment probability and explanatory factors, even if such a policy or strategy is not explicitly stated, but for example is merely observed as a correlation after the fact. Hence, the deficiency of the state of the art could affect training on any data that includes treatments that were not randomized, and thus it is potentially quite severe.

In view of the deficiency, the invention provides a method for utilizing the power of learning-capable systems while remedying these shortcomings. The invention provides a method for utilizing observational or retrospective data even when the impacts of explanatory factors on outcomes are complex.

Imputation of Incomplete Explanatory Data for Learning Capable Systems

A further aspect of the present invention concerns the utilization of evidence from original (individual subject) data when the data on explanatory factors is incomplete. The problem of incomplete explanatory data is important for learning capable systems. For example, training of a neural network generally requires complete data entries for each subject. However, available data sets—from retrospective studies or even from prospective clinical trials conducted at high expense—are often incomplete in the explanatory variables.

This problem may in particular arise in the aforementioned "disaggregation" of evidence, since a study "A" may fail to test a factor "X" known to play a role in other sources of evidence. Hence, factor "X" would be missing in the entire study A.

It is unsatisfactory simply to restrict the use of learning capable systems to those sources of evidence or those data sets that are complete in the explanatory variables. This restriction would constitute a very severe limitation on the use of learning capable systems, since data are often the most costly resource, and there may not be enough or even any complete data sets available for analysis. The procedure of simply ignoring (deleting from the data set) all explanatory factors for which there are incomplete data in some patients in order to render an incomplete data set complete is likewise unsatisfactory if the deleted factors have an important effect on outcome. The learning-capable algorithm would be denied access to information that it needs to make an accurate outcome prediction.

The simple and often-used procedure of "listwise deletion" (deleting all subjects with even one missing value of an explanatory factor) is in general unsatisfactory for the purpose of training a learning-capable system, for several reasons:

At best, a percentage of subjects and thus potential power is lost. This loss can be very serious even at modest missing data rates. For example, if there are 10 explanatory factors and a 5% missing rate for each factor, randomly distributed among the subjects, then the percentage of deleted subjects would be about 40%.

In the statistical context, listwise deletion is known to introduce bias, unless certain assumptions about the pattern of missingness are satisfied, these assumptions often being difficult or impossible to prove. There is no evidence that listwise deletion is any better for learning-capable systems.

Listwise deletion is only an option in training a learning-capable system, not in applications to new data: It is not an option to delete a subject with incomplete data if one requires the outcome estimate for this subject.

For application to training of learning-capable systems requiring complete data such as neural nets, substituting a value within the valid range for each missing value is a known alternative. Such a procedure is known as "imputation." Unfortunately, simple imputation methods such as substituting the univariate mean of said factor for the missing value (referred to in what follows as "mean imputation") or other univariate procedures are known from the statistical context to be unsatisfactory, because they may lead to a statistical bias, especially if missingness is correlated with factors which themselves are explanatory. For example, if there are correlations among the explanatory factors, the univariate mean is a poor guess for the value of the missing variable conditioned on what is known about the other factors. There is no proof or evidence that similar problems would not occur if mean imputation is used in training a learning-capable system.

Imputation algorithms known as "expectation maximization (EM)" offer a potential improvement, but it is known in the statistical context that the use of data imputed by EM to estimate a statistical outcome model fails to estimate the variance properly. Hence, the use of even a relatively advanced imputation method such as EM to pre-process the data used to train a learning-capable system lacks any mechanism for providing an indication of that part of the uncertainty of outcome estimation associated with uncertainty in the imputed values.

This lack constitutes a grave deficiency of the current state of the art of training of learning-capable systems. This deficiency of the current state of the art could have severe consequences, for example if the learning-capable system is intended for application in a decision support framework. The reason is that an underestimate of the uncertainty of an outcome prediction could lead to an underestimate of the risk of unusual outcome events (e.g., early relapse in breast cancer). If said unusual events are associated with very severe consequences (e.g., distant metastasis in soft tissue in breast cancer, which almost always leads to rapid death of the patient), then both the expected outcome and its uncertainty are important for determining the best intervention (e.g., therapy). An aspect of the present invention addresses a remedy for this deficiency.

Finally, the invention addresses the commonly occurring problem of training a learning-capable system in the case of explanatory data entries that were not originally recorded as missing, but whose values as recorded were incorrect. It also relates to the problem of detecting implausible data entries in an on-line system for data acquisition.

Special Data Acquisition Designs

A further aspect of the present invention concerns the utilization of evidence from original (individual subject) data for training a learning capable system to predict outcomes on the basis of explanatory variables when data acquisition is incomplete by design. An typical example of such a design is the so-called "case-cohort" design for a prospective clinical trial in which samples are collected at entry into the trial and conserved for possible future measurement. Suppose for example that 1. only a small group of subjects will suffer failures compared to the much larger group not suffering failures;
2. a subset of the proposed explanatory factors require very expensive measurements (e.g., either because valuable sample is consumed, or because the measurement itself is very expensive to perform);
3. all or part of this factor subset is thought to be very important in predicting which subjects will suffer failures Suppose for example there are N subjects and among them C "cases" with failures with $C \ll N$. In this case, one strategy would be to measure the subset of "inexpensive" factors on all N subjects, whereas the expensive factors would be measured on the cases as well as on a randomly selected subcohort of size S with $S \ll N$.

The invention relates to a method of training a learning-capable system for such an incomplete study design by introducing multiple stages of the learning capable system.

In one embodiment, the invention also relates to the case in which multiple, possibly competing risks $r=1, 2, \ldots$ are present, such that a number $C_r$ of "cases", occur for each risk, and in which different subsets of the factors are measured for each $C_r$ and for a corresponding subcohort $S_r$.

Reference

The invention also addresses the issue of providing the risk of a subject relative to any reference subject that can be characterized by specified explanatory factors. Defining risks with respect to such a reference subject would be especially useful if for example the distribution of outcomes of subjects similar to the reference subject is well known in the population in question, but the learning-capable system was trained on a different population.

Lack of Method Up to Present

At present, there is no satisfactory objective methodology meeting the above described needs and requirements.

It is the problem underlying the invention to provide a method for training at least one learning capable system with improved objectivity.

BRIEF SUMMARY OF THE INVENTION

This problem is solved by the method of claim 1. This method for training at least one learning-capable system comprises the steps of:

providing a predetermined training data set corresponding to a predetermined number of subjects comprising a predetermined input data set and a predetermined outcome data set, augmenting the input data set and/or the outcome data set, and training each learning-capable system using the augmented input data set and/or the augmented outcome data set.

By augmenting the input data set and/or the output data set, additional information, e.g. additional explanatory variables, is taken into account and used when training the learning-capable system. In this way, the trained learning-capable system has improved objectivity.

Advantageously, the step of augmenting the input data set comprises the steps:

estimating propensity score data for each subject depending on its input data, dividing the propensity score data into at least two strata, assigning each subject to a stratum, and augmenting the input data of each subject by its propensity score data and/or its stratum data.

Therefore, the propensity scores are categorized and these categories are called "strata". This categorization has the effect that the propensity scores of the subjects are taken into account. In particular, this method overcomes the deficiencies of the prior art as discussed in the section "Outcomes research and observational data".

Preferably, the training step comprises the step of optimizing the operating point parameters for each stratum. This results in an operating point correction in each stratum which further improves the objectivity of the trained learning-capable system.

According to a preferred embodiment, the operating point parameters are optimized such that the median of all output data vanishes for each stratum.

According to a preferred embodiment of all previously described methods, the augmenting step comprises the step of:

generating a plurality of augmented training data sets by augmenting the input data set using a statistical model.

In this embodiment, it is possible to train a learning-capable system having incomplete input data of subjects. Thus, on the one hand, a source of bias can be removed or reduced, on the other hand, a loss of power due to a reduced number of subjects is avoided. In particular, this method overcomes the deficiencies of the prior art as discussed in the section "Imputation of incomplete explanatory data for learning-capable systems".

Preferably, this method is used for training at least two learning-capable systems, wherein the training steps comprises the steps of:

training each learning-capable system using a subset of the plurality of augmented training data sets, constructing scores for each outcome for the trained learning-capable system, and determining characteristics of the distributions of the scores for each subject.

Thus, the influence of the randomness in the input data is characterized. The subset of the plurality of augmented training data sets can also be all augmented training data sets. By training a plurality of learning-capable systems, a library of trained learning-capable systems can be obtained. The training of at least two learning-capable systems can also be interpreted as training at least two instances of a learning-capable system.

It is advantageous to augment the input data set using a generalized Markov chain Monte-Carlo method.

According to a preferred embodiment of all previously described methods, the augmenting step comprises the steps of:

providing a further learning capable-system and a further predetermined training data set comprising a further predetermined input data set and a further predetermined outcome data set, training the further learning-capable system using the further predetermined training data set, and augmenting the input data set by at least one additional variable taken from the further input data, further outcome data and/or internal output data obtained from the trained further learning-capable system.

In this way, the input data is augmented using additional variables resulting from the training of a further learning-capable system. With this method, it is possible to combine several learning-capable systems. This can even result in a multi-stage learning-capable system. However, the further predetermined training data set can be partly or fully identical to the training data set.

According to a preferred embodiment of this method, the additional variables comprise all further input data and all further outcome data of a subset of subjects of the further training data set.

According to a preferred alternative, the additional variables comprise all further input data, all further output data and all internal parameters of the trained further learning-capable system.

According to a preferred embodiment of all previously described methods, the outcome data of the training data set is time-dependent and the augmenting step comprises pre-transforming the time variable of the training data set in such a way that the hazard rate with respect to a predetermined outcome is a predetermined function of the time variable. In this case, the additional information that is taken into account is a transformed time variable. Thus, the number of coefficients required to represent the time-variation of said outcome may be reduced, or the interpretation of said coefficients may be simplified. For example, the time variable is transformed in such a way that the hazard function is a constant or nearly constant function of the time variable.

Advantageously, the underlying hazard model for the occurrence of an event of type k for training a learning-capable system according to one of the above described methods using a training data set with time-dependent outcome data is of the form $$\lambda_k(t|X) = \lambda_{k0}(t) h_k(t|X, \phi_1, \phi_2, \ldots, \phi_P)$$

with X the input data for each subject and with $$h_k(t|X, \varphi_1, \varphi_2, \ldots, \varphi_P) = \exp\left[\sum_{l=1}^{L} B_l(t) \binom{NN_{kl}(X) -}{OP_{kl}(\varphi_1, \varphi_2, \ldots, \varphi_P)}\right],$$

wherein $OP_{kl}(\phi_1, \phi_2, \ldots, \phi_P)$ are the operating point parameters for the propensity score data $\phi_1, \phi_2, \ldots \phi_P$, $NN_{kl}(X)$ denotes the output of the learning-capable system for input data X and the functions $B_l(t)$ are chosen appropriately.

Preferably, the operating point parameters are of the form $$OP_{kl}(\phi_1, \phi_2, \ldots, \phi_P) = OP_{kl1}(\phi_1) + OP_{kl2}(\phi_2) + \ldots + OP_{klP}(\phi_P)$$

This form is not restricted to the case of time-dependent outcome data.

The present invention also provides a method for using a learning-capable system trained according to one of the methods described above using the input data of a subject, characterized in that the outcome is corrected with respect to a predetermined reference subject. This allows a comparison of a new subject with a reference subject.

Preferably, the following hazard function is used for this correction:

$$H_k(t, X, X_0) = \exp\left[\sum_{l=1}^{L} B_l(t)(NN_{kl}(X) - NN_{kl}(X_0))\right]$$

wherein X denotes the explanatory factors of the subject and $X_0$ denotes the explanatory factors of the reference subject.

The present invention also provides a method for using at least two learning-capable system trained according to one of the methods for training at least two learning-capable systems described above using the input data of a subject, comprising the steps of:

presenting the input data of the subject to each of the learning-capable systems and constructing a score for the output data obtained from the learning-capable systems.

The present invention provides a method for creating a composite training data set comprising the steps of:

providing an aggregated evidence data set, disaggregating the aggregated evidence data set to obtain a disaggregated training data set with virtual subjects, and merging the disaggregated training data set with a further training data set.

Given an aggregated evidence data set, this method yields a composite training data set with a number of possibly virtual subjects for training a learning-capable system. A composite training data set obtained in this way is a composition of at least two training data sets. This method is particularly useful to obtain an input data set for training a learning-capable system according to one of the above described methods. Nevertheless, this method for creating a composite training data set can also be used for training a learning-capable system without an augmenting step as described above.

According to a preferred embodiment, the merging step comprises the step of choosing a real training data set as the further training data set.

In a preferred embodiment, the disaggregation step comprises the step of assigning at least a value of one auxiliary variable to each virtual subject of the disaggregated training data set. These auxiliary variables can be nominal, ordinal or metric auxiliary variables.

Preferably, the merging step of the previously described methods comprises the step of transforming the data of the disaggregated training data set and the another training data set to a common scale.

According to a preferred embodiment of all previously described methods for training at least one learning-capable system, the predetermined training data set is provided using one of the previously described methods for creating a composite training data set.

According to a preferred embodiment of all previously described methods, each method is used to assess the risks in the case of pregnancy or breast cancer. This method can be used to select a treatment having the greatest expected benefit for a comparable population.

The invention also provides a computer program product directly loadable into the internal memory of a digital computer, comprising software code portions for performing the steps of one of the method described above, when said product is run on a computer.

The invention also provides a computer program product stored on a medium readable by a computer, comprising computer readable program means for causing a computer to perform the steps of one of the method described above, when said product is run on a computer.

BRIEF DESCRIPTION OF THE DRAWINGS

Further embodiments and advantages of the invention are described with reference to the drawings. In the drawings.

DETAILED DESCRIPTION OF THE INVENTION

Method for Evidence Disaggregation and Synthesis

Specifically, the invention meets the need for improved objective evidence synthesis by 1) constructing one or more composite data sets from disaggregated training data for each known source of evidence and 2) training one or more neural networks or other learning-capable systems to score outcome(s) based on said composite data sets.

"Disaggregated training data" is defined for the invention as a representation of evidence approximating the known relationship between characteristics and outcome(s) that is originally available to the system only in aggregated form ("aggregated evidence") in terms of a realization of a statistical distribution of the characteristics of the subjects, together with a realization of the distribution of outcomes conditional on said characteristics, where said conditional distribution is represented according to the statistical model implied by said aggregated evidence.

Figure 1:
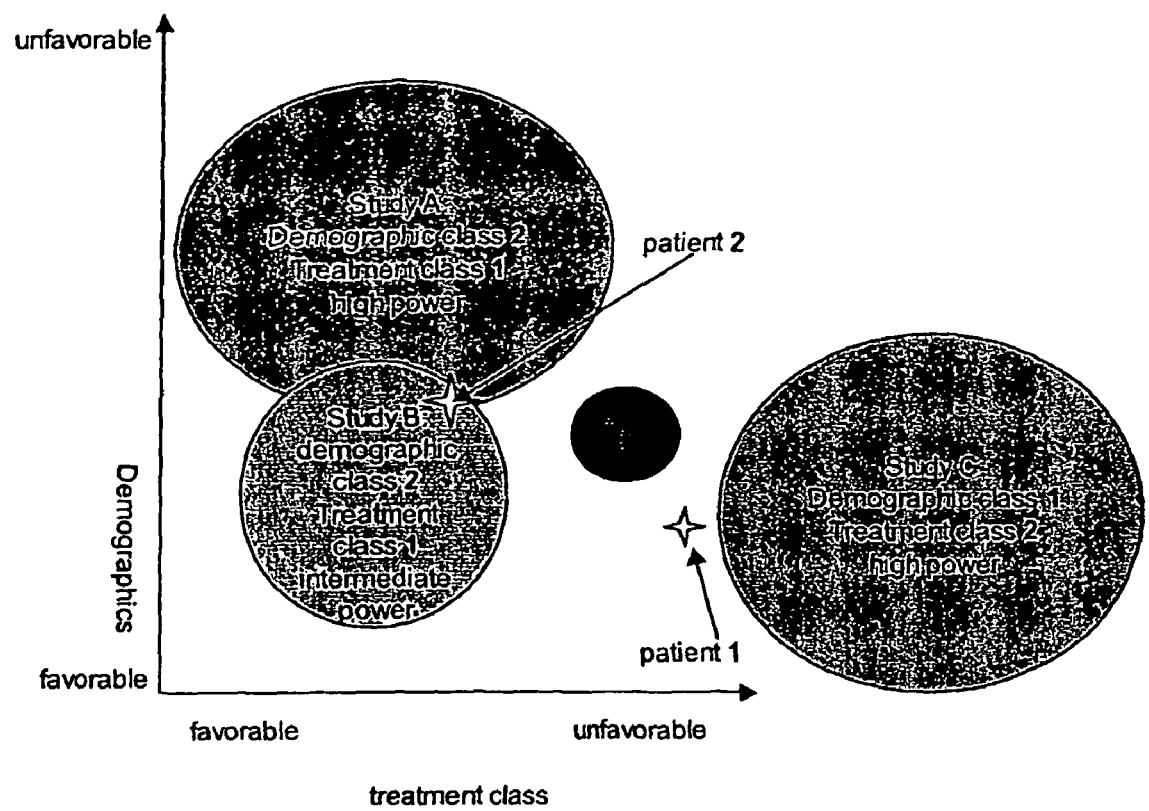
FIG. 1 shows a schematic diagram illustrating the study assignment problem.

An example of a typical intended application of the invention is schematically illustrated in FIG. 1.

The diagram illustrates two situations typical of risk assessment for decision support applications. Patient 1 belongs to a population with unfavorable standards of care and favorable demographic characteristics, so that the population is situated between one large study (Study C) and one small study (Study D). Patient 2 belongs to a population with characteristics covered by both studies A and B.

For patient 1, one alternative would be to use only the study centered nearest to the patient (in this case, D). However, there are two difficulties associated with this alternative:

1. Study C was much larger than study D and, all other things being equal, provides more reliable risk assessment.
2. If we consider a sequence of hypothetical patients with constant risk factors but varying demographics/treatment gradually approaching Study C, we would expect our model to provide a smooth transition in risk assessment.

The invention provides a means for remedying these difficulties by allowing interpolation in the space of risk models. The interpolation takes into account the reliability of the original information to the extent known.

For patient 2, it is not obvious which study to use, but it could happen that his or her risk factors correspond to a regime in which the models of the two studies give highly concordant risk assessment. (Due to correlations among risk factors, concordance does not require that the coefficients in the statistical models agree, but only that they give similar scores.) In this case, it essentially does not matter which model is used. However, if for this patient the two applicable models are not concordant, the invention provides a means for fusing the information. Hence, the invention provides a means for giving a unique result when there are redundant and possibly not entirely concordant sources of evidence, again taking into account the reliability of the original information to the extent known.

The invention provides an empirical method for evaluating performance as follows: Suppose that we initially train the evidence synthesis tool according to the method of the invention without utilizing the information in one of the studies, say the small study D. According to the method of the invention, we may then consider a hypothetical population of patients who actually are covered by the small study D above and tabulate measures of concordance between the predictions of the risk assessment tool and the model of study D. Hence an added benefit of interpolation capability of the invention is a means for performance evaluation.

Finally, a typical question for sensitivity analysis might be phrased as follows: how important are demographic factors in modulating the risk of a patient with respect to an outcome of interest? Could unfavorable demographic factors help define a larger (or smaller) group that are at high risk than would have been inferred from a particular study? The interpolation capability of the invention provides a means for improving sensitivity analysis by permitting a virtual variation of population factors.

Method for Incorporation of Prior Knowledge and Synthesis of Real and Aggregated Data The invention also relates to the synthesis of real training data and aggregated evidence training data to train a learning-capable system such as a neural network. Specifically, the invention accomplishes this need by 1) constructing one or more composite data sets, each of which includes both the real training data and disaggregated data approximating the known relationship between characteristics and outcome(s) for each aggregated source of evidence and 2) training one or more neural networks or other learning-capable systems to score outcome(s) based on said composite data sets.

The invention also relates to a method for incorporating prior knowledge into the training of a neural network or other learning-capable system: The synthesis of real and disaggregated training data indeed constitutes a method for incorporating prior knowledge into the training of a neural network or other learning-capable system, where the "prior knowledge" is defined as a relationship between characteristics and outcome coded in the form of aggregated evidence. It will be seen that the quality of the synthesis performed in this way offers the benefit of consistency with the well-known "Bayes theorem" of statistics.

Method for Complex Modeling of Observational Data

For many of the above problems, insufficient evidence from carefully conducted, randomized trials is available. In follow-up observational data primary in breast cancer, for example, the decision for administration of adjuvant systemic endocrine therapy or chemotherapy reflects guidelines and policies that have evolved over time and also can depend systematically on the study population. Moreover, outside of randomized trials, the probability of receiving a given treatment usually depends on explanatory factors in a manner that can vary from one study to another. Such dependencies are examples of "confounders," and they falsify or "bias" inferences on treatment efficacy. For example, in breast cancer, patients with many affected lymph nodes have usually been those most likely to receive chemotherapy, and hence a univariate comparison of relapse-free survival between patients receiving and not receiving chemotherapy would often find that chemotherapy is associated with poorer survival, the reason being in this case that selection bias is stronger than the benefit of therapy.

Even "randomized" clinical studies often face the problem that some patients randomized to the control group will choose therapy and vice versa. Hence, a simple comparison of "treated" and "untreated" groups is not necessarily free of selection bias. Moreover, observational data are often relatively inexpensive to obtain, and they may be more representative of outcomes in an ordinary clinical setting.

In fields outside of medicine, especially in public policy, business, and finance, one is often forced to use data collected through the observation of systems as they operate in normal practice.

Methods of outcomes research have been developed for assessing treatment effects from observational data. However, methods available up to now do not address the need to model complex impacts of explanatory factors and treatments on outcomes, including interactions of explanatory factors among themselves and with treatments (in clinical practice the latter interactions include "predictive impacts" of factors). More generally, dependencies of treatment on explanatory variables can affect the statistical relationship between explanatory factors and outcomes so as to render the relative impacts of explanatory factors found in one observational study false when applied to a new situation with a different treatment strategy, or a situation in which the object of modelling is to find an optimal treatment strategy among proposed alternatives A method for remedying these shortcomings—even when the impacts of explanatory factors on outcomes are complex—is provided by the invention.

Method for Use of Missing Data and Combination of Multiple Instances of Learning-Capable Systems The invention also relates to a method for training learning-capable systems such as neural networks of the type that relate outcome to explanatory characteristics even in the presence of missing data in said explanatory characteristics. The invention accomplishes training with missing data by 1) constructing many "realizations" of data collectives imputed according to a method that models the uncertainty in imputed values, such as a generalized Markov-chain Monte-Carlo method, 2) training one or more instances of the learning-capable system for each said realization, 3) constructing scores for each outcome for each such trained system, 4) providing mean, median, and other statistical characteristics of the distributions of said scores for each subject. This method will be referred to in what follows as "multiple imputation for a learning capable system".

In an embodiment of the invention, output scores from a plurality of instances of trained neural networks are combined into a composite score (for example, by taking the mean or median over the instances) together with one or more measures of statistical variation among these scores so as to provide internal measures of uncertainty or reliability. This embodiment also includes the case in which scores of different architectures or even different learning-capable systems are thus combined.

This embodiment of the invention is specified below in an example in which the learning capable system is a neural network.

Method for Training a Learning Capable System for a Special or Restricted Data Acquisition Design Suppose analysis using a learning-capable system that requires or prefers complete data is to be performed for a study design as described above with N subjects, among which there are C "cases" with failures, such that C<<N. In this case, one strategy would be to measure the subset of "inexpensive" factors on all N subjects, whereas the expensive factors would be measured on the cases as well as on a randomly selected subcohort of size S with S<<N. Let X be the covariates measured for all patients, and let Z be the expensive factors measured only on the C&S subsets.

The state of the art is quite unsatisfactory, because it offers the choice between 1. training on the entire set N but ignoring the expensive factors Z
2. training on the C&S set with expensive factors Z, but omitting the remaining large group of patients The invention in the preceding embodiment offers the option of multiple imputation for training a learning capable system, in this data environment. Note however that the percentage of imputed values of Z would need to be much larger than the number of known values of Z, and that the statistical imputation model would have to rely on the known explanatory information X for those subjects with missing Z; however, the case of greatest interest for such designs is precisely the opposite one in which the X factors consist of measurements that are likely to be only weakly correlated with the Z factors.

It may also happen that multiple, possibly competing risks r=1, 2, ... are present, such that a number $C_r$ of "cases" occur for each risk, and in which different subsets of the factors are measured for each $C_r$ and for a corresponding subcohort $S_r$. The state of the art is also unsatisfactory for this situation.

Extension of Embodiments to Multiple Instances

Any procedure that combines multiple instances of learning-capable systems to obtain output is also defined as a "learning capable system" in the sense described above. This definition includes not only the case in which different instances of a particular kind of learning capable system are combined (such as a feed-forward neural network of a particular topology), but also different topologies of a learning-capable system (e.g., neural nets with different numbers of hidden nodes) or even entirely different learning-capable systems (e.g., a neural net and a recursive partitioning algorithm) are combined, provided only that an identical functional relationship (underlying statistical probability model) relating output scores to outcome probability is associated with each system or instance.

Extension of Embodiments to a Pre-Transformation of the Time Variable.

If, in data to be presented to a learning-capable system, the hazard rate of a population or reference subgroup with respect to an outcome or to a risk can be determined to deviate significantly from a constant hazard rate, then the invention provides for the possibility of pre-transforming the original variable t≧0 used to denote the time of occurrence of events or observations according to any invertible (monotonic) transformation procedure that results, for example, in a more nearly constant hazard rate for the population or subgroup of interest. One method is to fit the parameters $\Lambda$ and $\gamma$ of the Weibull distribution, which is associated with a time-dependent hazard of the form $$\lambda(t;\Lambda,\gamma)=\Lambda\gamma t^{\gamma-1}$$

(where $\Lambda$ and $\gamma$ are both positive), to the outcome data and to introduce a new time variable such as $T=t^\gamma$. This pre-transformation is favorable for training because the number of coefficients required to represent the time-variation of said risk may be reduced, or the interpretation of said coefficients may be simplified.

Embodiments in Breast Cancer

In a particular embodiment in breast cancer, the method of the invention is used to assess 1, 2, 3, 4, 5, 8 and 10-year risks of death, relapse, distant relapse, distant relapse in bone, distant relapse not in bone, local or loco-regional relapse, etc. In a specific embodiment, said factors include any of the following:
 number or status of affected lymph nodes
 tumor size or classification
 grade
 age
 estrogen receptor
 progesterone receptor
In another specific embodiment, said factors include either or both of
 the level of urokinase-type plasminogen activator (uPA)
 the level of its inhibitor plasminogen activator inhibitor-1 (PAI-1),
In still another specific embodiment, said factors include proposed adjuvant therapies such as
 adjuvant chemotherapy of any kind
 adjuvant endocrine therapy of any kind
and combinations or the lack thereof.
 In still another specific embodiment, said factors include
 measurements relating to Her2 status and/or
 proposed Trastuzumab therapy.
In a specific embodiment, the invention is used to select a treatment having the greatest expected benefit for a comparable population. "Expected benefit" in this embodiment is defined as the average overall survival and/or disease-free survival balanced by the negative effect on the quality of life due to the side effects of a particular cancer treatment in a comparable population.

Embodiments in Pregnancy Complication Prediction

In particular embodiments, the method of the invention is used to assess risks of pregnancy complications such as preeclampsia, foetal growth restriction or spontaneous preterm birth, including severe complications such as "HELLP" syndrome or early onset disease in pregnant women, particularly in nulliparous women, on the basis of objective factors commonly known or determined during the first 25 weeks of pregnancy. In specific embodiments, said factors include any or all of the following:
 Primipatemity and Sperm Exposure
 Family History of Preeclampsia
 Early Pregnancy Blood Pressure
 Cigarette Smoking
 Stress
 Uterine Artery Doppler Waveforms
 Obesity
 Insulin Resistance
In a further embodiment, said factors include any or all of
 Lipids
 Glycoproteins such as Fibronectin
 Angiogenic proteins such as Vascular Endothelial Growth Factor (VEGF), Placental Growth Factor (PIGF).
 Tumour Necrosis a
 Thrombophilias
 Plasminogen Activator Inhibitors (PAI)
 Insulin Growth Factor Binding Protein-1 (IGFBP-1) Leptin
 Transforming Growth Factor β (TGFβ)
In a specific embodiment, the invention is used to select a treatment having the greatest expected benefit for a comparable population of pregnant women. "Expected benefit" in this embodiment is defined by utilizing the decrease in risk of one or all of said pregnancy complications due to therapy to compute an improved expected quality of life in a comparable population, balanced by negative effects on quality of life due to the side effects of a particular treatment in a comparable population, and possibly balanced by other factors of interest to the patient.

EXAMPLES

As a prerequisite for examples of the method of the invention, the function of a neural net is specified here for the case of in the form of a multi-layer perceptron as an example of a learning-capable system.

Operation of Neural Nets

Neurons as Functions

Each neuron receives a stimulus S, processes this via a prescribed activation function F(S) and produces a corresponding response A=F(S), which is supplied to all subsequent connected neurons. In the specified embodiment, the activation function is the hyperbolic tangent. The invention can be utilized for any appropriate activation function such as the logistic function.

Transformations and Input Neurons

The factors are initially transformed if required by a univariate transformation to be of order unity. This can always be achieved by a function of the form $$X_j=\tan h[(x_j-x_{Median})/x_Q] \tag{1a}$$

That is, the median $x_{Median}$ is subtracted, and the value is scaled by a factor $x_Q$. Values above the median are scaled by the 75%-percentile, values below the median by the 25% percentile, and the function tan h is applied to the result.

The input neurons have a static function and are therefore implemented as arrays which simply transmit the transformed values. The tan h-function of Equation (1a) can be regarded as an input activation function.

Hidden Neurons

The output of the hidden node (or neuron) h for subject j is desired. If the hidden node is inactive, the output is zero in the specific embodiment. The hidden node h is first checked to determine whether it is active. If so, the inputs to h are multiplied by the appropriate weights and summed. More precisely, the signal to h is the weighted sum $$z_h(j) = \sum_i w_{ih} X_i(j), \tag{1b}$$

where $w_{ih}$ is the weight of the connector from input neuron i to output neuron h, and $X_i(j)$ is the scaled response of the i-th input neuron. The response of the hidden neuron h is $$Y_h(j) = F_h(z_h(j) - b_h) \tag{1c}$$

Here, $b_h$ is the operating point (otherwise known as the "bias") of the hidden neuron h, which in practice is optimized computationally like any other weight of the network. In the specific embodiment, the nonlinear activation function $F_h$ is the hyperbolic tangent.

Output Nodes

The output of the output node (or neuron) i for subject j is desired. If the output node is inactive, the output is zero in the specific embodiment. If active, connectors could reach the output node o both from the hidden layer and directly from the input layer. For each active connector, the inputs are multiplied by the appropriate weights and summed.

A signal $z_o$ is first constructed, and then the operating point $b_o$ of the output neuron o is subtracted. Finally, the activation function of o is applied to this result. The output $O_o(j)$ is thus given by $$z_o(j) = \sum_i w_{io}(X_i(j) - c_i) + \sum_h w_{ho} Y_h(j) \tag{2a, b}$$

$$O_o(j) = F_o(z_o(j) - b_0)$$

In the specific embodiment, the activation function of the output layer is taken to be the identity function. In the specific embodiment, the operating point $b_o$ is not freely optimized, in contrast to the hidden layer, but rather chosen such that the median signal of all output neurons is zero. This choice does not restrict generality and reduces the number of parameters to be optimized.

Learning Capability

The learning capability of the neural network resides in the ability to optimize or prune the weights in the above descriptions during training, thus achieving a representation of the relationship between explanatory factors and outcomes. By analogy, another learning-capable system is included in the methods of this invention if
- it can represent the required class of relationships between explanatory factors and outcomes, and
- a sequence of operations is defined for optimizing or removing parameters to improve the performance of an appropriate objective function.

Specification of Method for Evidence Synthesis (Including Incorporation of Prior Knowledge and Synthesis of Real and Aggregated Data)

Figure 2:
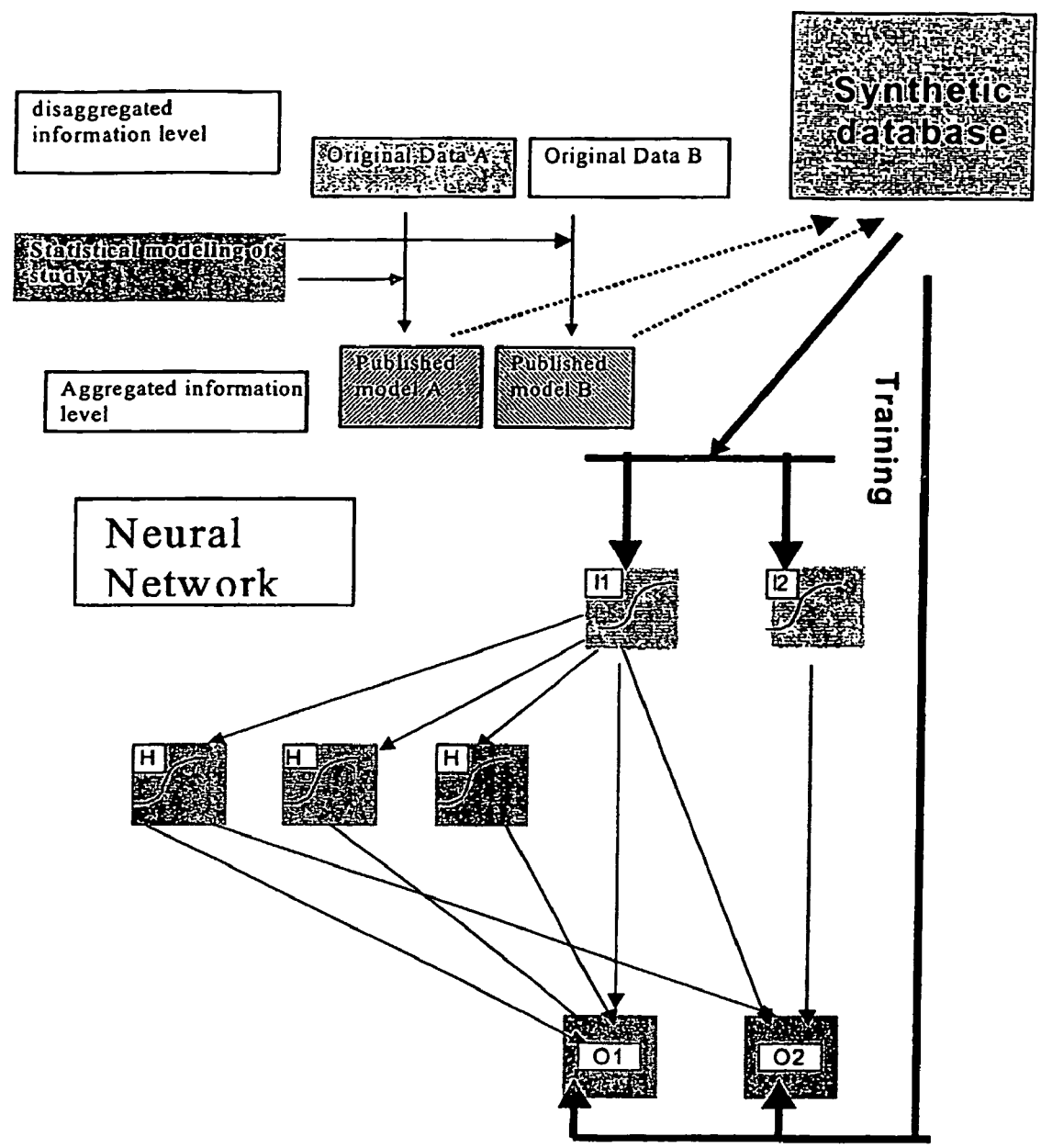
FIG. 2 shows a schematic diagram illustrating a training of a neural network for evidence based risk assessment synthesis.

These embodiments of the invention for evidence synthesis are schematically illustrated in FIG. 2. The original data on which the studies A and B are based is not accessible to train the network. By disaggregation (dotted lines in figure) and merging, composite training data sets are created. The composite data sets are used to train neural networks (indicated by bold lines and arrows). If original data is available, it can be merged directly with the composite database, by-passing the disaggregation step.

The procedures are specified in the following paragraphs and illustrated in an example below.

Disaggregation Step

The disaggregation step begins with existing evidence compiled in the form of "studies".

In a particular embodiment, we illustrate the case of a proportional hazards (exponential time dependence) model of survival data with explanatory data distributed according to a multivariate Normal distribution. This distribution is characterized by the vector of means and the variance-covariance matrix. Other distributions are analogous.

After acquiring study information, patterns are generated for each study as follows.

Obtain information required to generate explanatory part of patterns
1. Query and store number of patterns (virtual subjects) to be generated
2. Query and store means and variance-covariance matrix of explanatory variables
3. Normalize variables
4. Diagonalize variance-covariance matrix
5. Eigenvectors define transformed explanatory variables which are independent realizations of a univariate normal distribution Generate patterns
6. For each pattern, generate random independent (univariate) Normal deviates for each explanatory variable
7. Invert transformation to obtain original variables Query parameters of study and store these:
1. Median survival time (natural survival time without treatment, or with a reference treatment)
2. Length of study
3. For each reported explanatory variable, query hazard ratio associated with variable in model. Some explanatory variables that are included for later steps may not be significant in the study. These variables are carried but have no impact on risk assessment from the study. They may be thought of as being assigned hazard ratio one.
4. Treatment probabilities if reported
5. Baseline/average treatment effects if reported
6. Store this information in the form of a hazard model Generate follow-up (outcome) data
1. For each virtual subject, compute hazard from stored hazard model
2. Generate exponential deviates
3. Divide by risk and re-normalize to parameters of study (survival times, censoring)
4. Model censoring and record failures (e.g., relapses) observed before censoring, else subject is censored Output virtual data set to a storage medium Each of the individual steps listed above can be part of a computer program. In a preferred embodiment of the invention, queries are performed by appropriate software templates that prevent missing or inadmissible responses, or the query is performed automatically as a look-up in a database.

In another embodiment, step 6 is replaced by an analogous step if deviates for variables are known to be distributed according to another (possibly multivariate) statistical distribution. Preferred examples include the binomial distribution and the uniform distribution. In a further embodiment, a transformed variable distributed according to one of these distributions is obtained from original variables by an invertible pre-transformation. In a preferred embodiment, this pre-transformation includes assignment of fractional ranks. Hence, using an appropriate transformation, the method can be applied for a continuous variable with any specified distribution having an invertible transformation to a uniformly distributed variable.

In an embodiment, the number of patterns generated is equal to the number of subjects in the original study. In another embodiment, multiple instances of the data set with hazards drawn from a Normal distribution of the reported study results are used. For each explanatory factor, the mean of said Normal distribution is obtained from the reported hazard ratio, and the standard deviation is obtained from the reported confidence interval or other uncertainty estimate of the study. Each said standard deviation can be computed from said reported confidence interval. Each said instance of the data set is generated using random deviates drawn from these normal distributions of hazard.

If the outcome data are not survival data, but simply binary outcome data, then the procedure is simpler and could be inferred from the above.

Construction of Composite Data Sets by Merging

One or more composite data sets are constructed by merging the data of different sources of evidence. In one embodiment, multiple instances of composite data sets are constructed by sampling from multiple instances of disaggregated data sets (disaggregated data). In another embodiment, multiple instances of composite data sets are constructed by multiple re-sampling or bootstrapping from real or disaggregated data sets.

In one embodiment of the method, the populations of the available studies (i.e., evidence) are characterized by one or more auxiliary variables (nominal, ordinal, or metric) as illustrated in FIG. 1. For each source of evidence, the values of said auxiliary variables are assigned to all subjects of the corresponding data set. In a standard spreadsheet program, with individual subjects corresponding to rows, the auxiliary variables would correspond to new columns.

From each source of evidence to be considered, there will be one or more data sets available including explanatory variables and outcomes. Some of these data sets contain original data, others disaggregated data. The explanatory and outcome data of all data sets are first transformed to a common scale, if a common scale was not originally present. In one embodiment, an approximately common scale is achieved by a fractional rank transformation of all explanatory variables.

Each subset of outcomes and explanatory characteristics is considered separately as required for application. "Explanatory characteristics required for application" are defined as the set of variables that are to be measured or queried in new subjects. "Outcomes required for application" are defined as the outcomes that are to be utilized for new subjects. In a specific embodiment, a Markov model is used for decision support. Then the outcome information is that required for the Markov model.

The value of any explanatory variable for a new subject is transformed to the appropriate common scale.

In one embodiment, if a study did not include a required explanatory variable, or said required explanatory variable was included but the variable was not significant, then the variable is generated in the disaggregation step but has hazard one as explained in Step 3 of "query parameters of study . . . ." In another embodiment, sources of evidence are restricted to studies that included all required variables.

In a specific embodiment, the auxiliary factors describing disaggregated study populations include at least one ordinal or metric score relevant to outcome and varying among populations but not varying within a study or not included in the study risk model. In a clinical study, examples of such scores include: percentage of subjects having received an efficacious treatment (possibly multiple) or risk percentage or median survival of a specified reference group of the population. An example of a "specified reference group" in primary breast cancer is the group of node negative subjects with grade 1, median age, tumor size>2 cm, positive hormone receptor status.

In one embodiment, as a further auxiliary variable, one or more propensity scores (propensity for being treated) may be assigned to the real subjects as defined according to the methods of the invention. For the disaggregated data, an average propensity score may be computed from the known percentage of subjects receiving the treatment.

In a preferred embodiment, possible missing explanatory data in real data sets is multiply imputed by the method of the invention and supplied to the learning-capable system.

Synthesis Step (Training)

For each composite data set obtained by one of said methods, a neural network or other learning-capable system is trained using patterns consisting of the values of explanatory variables as well as the auxiliary (population) variables and the outcomes. In a preferred embodiment, a system with supervised learning is employed. In a specific embodiment, a neural network with multi-layer perceptron form is trained, where the outcome scores of subjects are determined by the outputs of the network according to a specified model, and the inputs to the neural network are the values of explanatory variables as well as the auxiliary (population) variables, such that for a new subject with specified values of explanatory and auxiliary variables, an assessment of outcome would be provided by the trained neural network.

The invention provides for the case of a nominal auxiliary variable as follows:

In one embodiment of the invention, multiple binary variables are defined for each possible attribute and used as ordinary input nodes of the neural network or other learning-capable system.

In a preferred embodiment, a stratified neural net is trained as defined and described below. Each possible value of the nominal variable corresponds in this case to a stratum. Multiple dimensions of strata are permissible. With each stratum there is associated a "stratum bias" (defined as a correction to the reference score) as described below.

The invention provides for the case of metric or ordinal auxiliary variables as follows.

In one embodiment, the metric or ordinal auxiliary variables are treated as input nodes just as the other explanatory variables.

In another embodiment, strata are defined for some or all of the metric or ordinal auxiliary variables, for example according to rank. A stratified neural net is then trained.

In a particular embodiment of the invention, output scores from a plurality of trained neural networks are combined into an average and/or median score together with one or more measures of statistical variation among these scores so as to provide an internal measure of uncertainty or reliability. This embodiment also includes the case in which scores of different architectures or even different learning-capable systems are thus combined.

In a preferred embodiment, the neural network or learning-capable system is trained as formulated in PCT/EP01/14411.

It will be seen that the procedure specified in the invention also provides a method for incorporation of prior knowledge into real data. The prior knowledge need only be expressible in the form of evidence as in a "study".

Example

The method of evidence synthesis is now illustrated by an example. We begin with two simulated "studies" of the same underlying disease. Tables 1a and b describe the probability model for the simulated explanatory factors (covariance matrix and means).

The "true" disease is assumed for the purposes of the example to have an untreated natural median relapse-free survival of 60 months. The two populations are assumed to have the same underlying risk dependence on some explanatory factors (columns 1 and 2 of Table 2), but the relapse-free survival is assumed to be affected by simulated "treatments" that have not been recorded. These unrecorded treatments are intended to mimic differences in population characteristics arising in real data such as differences in "standards of care".

The "true" log hazard of the underlying disease associated with each factor is listed in the third column of Table 2. The data of the two simulated studies are generated with equal simulated censoring mechanisms allowing a minimum observation time of 50 months for surviving subjects.

Hazard ratios of the two simulated studies are first computed by the standard proportional hazards model, which is the model most commonly used in the literature for censored survival data. In study A, there is no hidden treatment. The log hazard ratios computed by proportional hazards for Study A are listed in column 4 of Table 2.

TABLE 1a

The correlation matrix of the explanatory factors.

| factor | xlypo | xer | xpr | xage | xtum | xupa | xpai1 |
|---|---|---|---|---|---|---|---|
| xlypo | 1.000 | −0.060 | −0.094 | 0.028 | 0.415 | 0.020 | 0.049 |
| xer | −0.060 | 1.000 | 0.541 | 0.294 | −0.066 | −0.182 | −0.190 |
| xpr | −0.094 | 0.541 | 1.000 | 0.031 | −0.063 | −0.066 | −0.135 |
| xage | 0.028 | 0.294 | 0.031 | 1.000 | 0.038 | 0.018 | 0.003 |
| xtum | 0.415 | −0.066 | −0.063 | 0.038 | 1.000 | 0.031 | 0.062 |
| xupa | 0.020 | −0.182 | −0.066 | 0.018 | 0.031 | 1.000 | 0.543 |
| xpai1 | 0.049 | −0.190 | −0.135 | 0.003 | 0.062 | 0.543 | 1.000 |

In study B, there are two treatments, one of which is administered at random, the other of which is preferentially administered to subjects with higher values of "xlypo" and "xer". It is also assumed to be especially effective in subjects with higher values of xupa and xpai1. The log hazard ratios computed by proportional hazards for Study B are listed in column 5 of Table 2.

TABLE 1b

The means and variances.

| factor | mean | variance |
|---|---|---|
| xlypo | .50 | 0.071 |
| xer | .45 | 0.087 |
| xpr | .45 | 0.097 |

TABLE 1b-continued

The means and variances.

| factor | mean | variance |
|---|---|---|
| xage | .50 | 0.083 |
| xtum | .51 | 0.083 |
| xupa | .50 | 0.084 |
| xpai1 | .50 | 0.083 |

The entry "x" in Table 2 is equivalent to a log hazard ratio of zero but also implies that the factor was not significant in the proportional hazards model. It is seen that the differing treatments are associated with differing risk models even in the same underlying "disease." An approximate median survival was also estimated for each "study" from curves generated by the standard product limit method. Such an estimation procedure is similar to what would often be encountered in published evidence, where median survival would either be reported directly or inferred graphically.

In order to demonstrate the invention, the probability models of the explanatory factors and the risk models of studies A and B including respective estimated median survival were first disaggregated and synthesized as described above. As described above, in this embodiment of the invention, the auxiliary variables characterizing the populations of the studies could be characterized by nominal, ordinal, or metric variables. We give two examples in order to describe both the nominal and the ordinal/metric cases.

TABLE 2

Hazards (true and measured)

| factor | name | true log hazard | Study A | Study B |
|---|---|---|---|---|
| 1 | xlypo | 3.00 | 2.83 | 2.67 |
| 2 | xer | x | x | −0.32 |
| 3 | xpr | x | x | x |
| 4 | xage | −1.00 | −1.20 | −0.55 |
| 5 | xtum | 1.00 | 0.83 | 1.02 |
| 6 | xupa | 0.75 | 0.58 | 0.61 |
| 7 | xpai1 | 0.75 | 0.89 | 0.44 |

Figure 3:
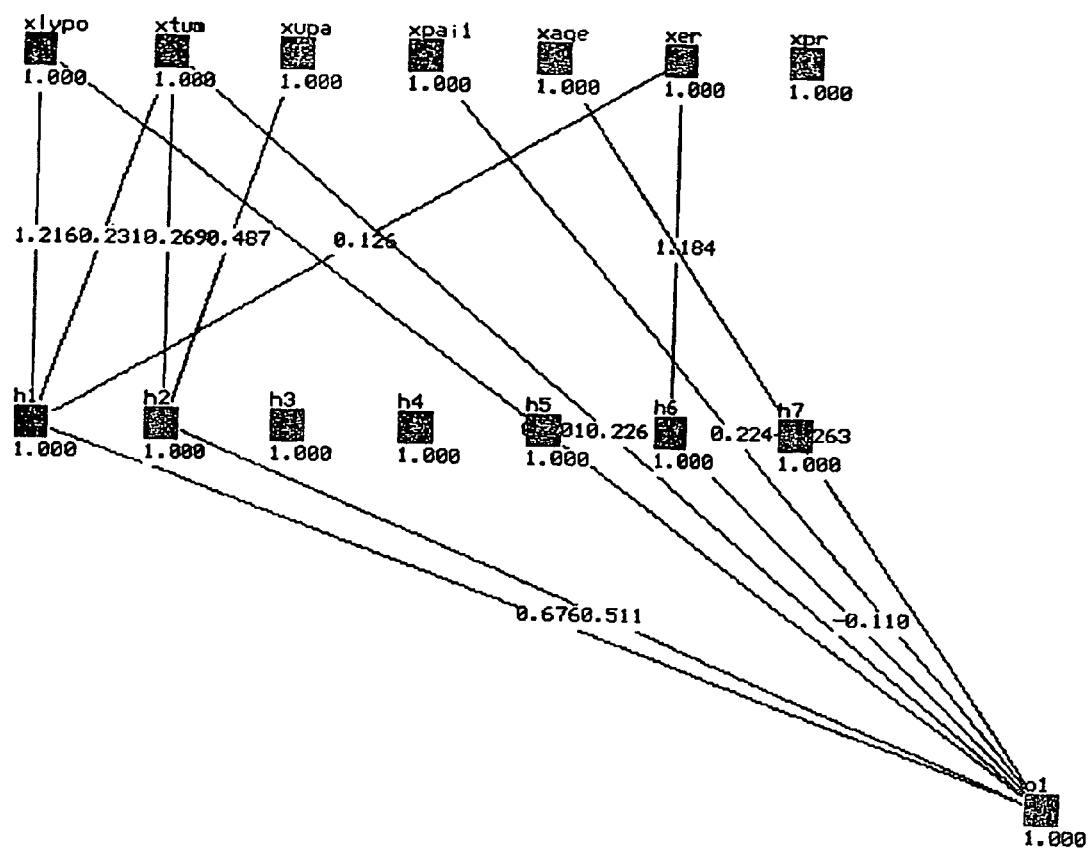
FIG. 3 shows a schematic diagram illustrating a stratified neural net for evidence synthesis.
Figure 4:
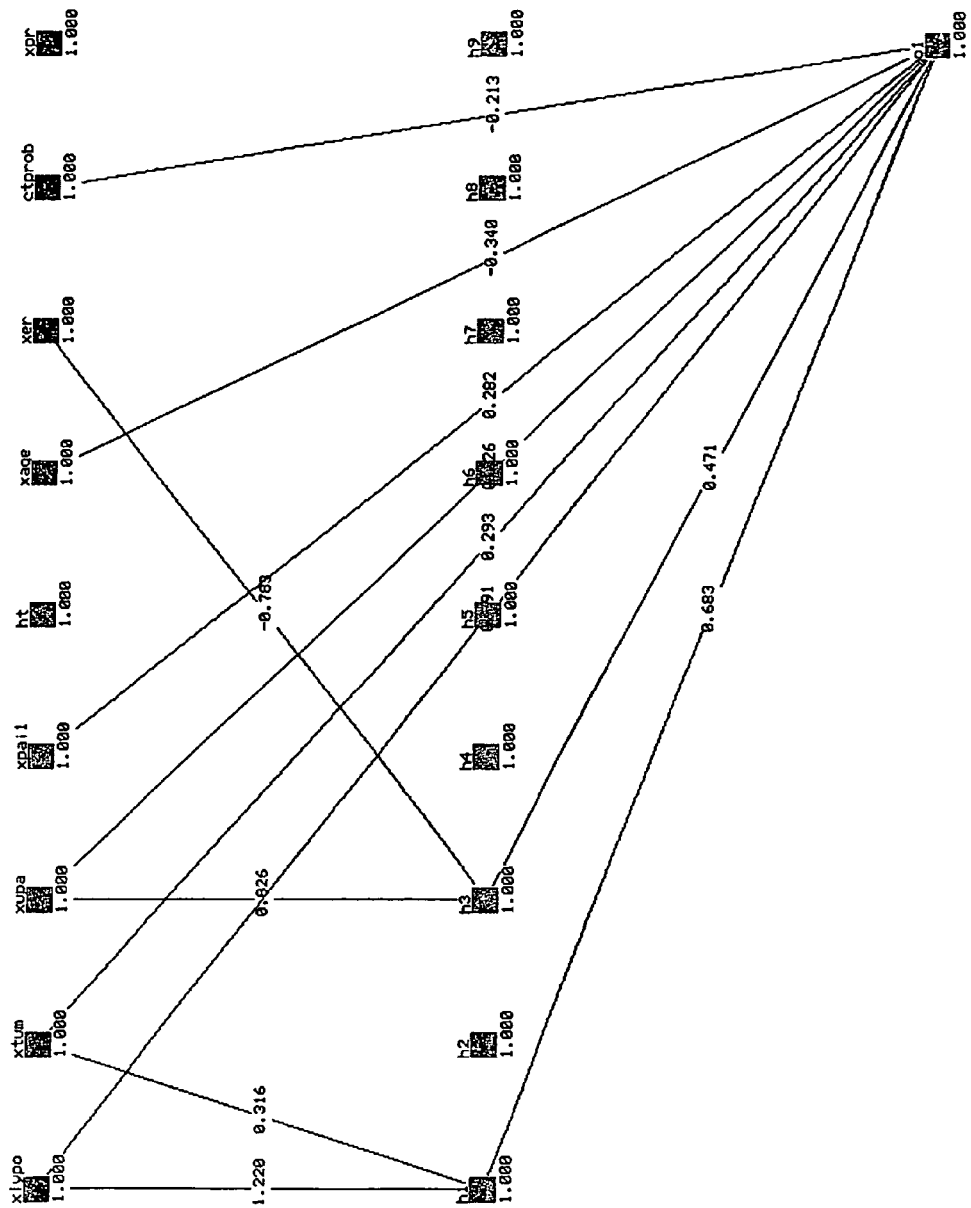
FIG. 4 shows a schematic diagram illustrating a neural net for evidence synthesis using auxiliary attribute as an input.

For the nominal case, a study identifier was appended to the separate data sets as described above, the data was merged, and a neural network was trained stratifying on the nominal identifier variable. The trained neural network was obtained by randomly choosing 50% of the patterns for training. The result is schematically illustrated in FIG. 3.

The connectors illustrated in the figure correspond to non-zero values of weights connecting the nodes in the feed-forward neural network as described above. In addition to the connections shown here, the risk model of the invention includes operating point corrections for each of the two strata as well as an overall time constant as described above.

In order to incorporate the operating point corrections into a risk model for "new" subjects, the invention includes a method for describing the risk of a subject relative to any given reference subject. In the example, the reference was defined as a subject with xlypo=0 and xtum=0, all other variables at their medians. With respect to this reference, adjusted risk scores including influence of the study can be computed and utilized in applications as described in earlier sections. Hence, the scores computed in this way solve the problem of evidence synthesis in this example for the case of nominal auxiliary data. Note that by defining a standard reference, a possible influence of a difference between the distributions of explanatory factors in the two strata on the respective operating point corrections is compensated for.

To illustrate the case of ordinal or metric auxiliary variables describing studies, the average probability of receiving one of the therapies was assumed to be known for each study, the other therapy still remaining hidden. This average probability can be regarded as either a metric or an ordinal variable. The value was appended to the separate data sets as described above and labelled "ctprob." The data of the two studies was again merged, and a neural network was trained including the new factor ctprob. The trained neural network was obtained as above by randomly choosing 50% of the patterns for training. The result is schematically illustrated in FIG. 3.

The resulting neural net solves the problem of synthesizing Studies A and B for an ordinal or metric auxiliary attribute (here "ctprob") describing the studies. In particular, treating ctprob as a metric variable, the method of this example may be applied to outcome assessment even for "new subject" belonging to a third population characterized by a value of ctprob differing from those of Studies A and B. The variable ctprob is associated with reduced risk according to the neural network in this example, conforming to expectations.

The invention provides for a method of referring the outputs of the neural network to any specified "reference subject" (rather than to the median of the merged set) as described earlier.

One can test the performance of a neural net trained as above on either real data or disaggregated data from a third study.

Specification of Method for Complex Modelling Including Outcomes Research

The invention provides a method for addressing the problem of bias in complex modelling of the impact of explanatory factors (including therapies) on outcomes based on data from observational study data; this is achieved by introducing a variable operating point correction into the output layer of a learning-capable system (e.g., a neural network of the multilayer perceptron topology). The invention thus provides a means of adjusting training for confounding factors and improving generalization of outcome scores, even if the treatments in original data used for training depended on explanatory factors. The method also relates to training of a learning capable system with any nominal explanatory data.

For the case of survival data, the method is specified as follows:

Hazard Model

Assume that survival data is observed for J subjects as follows: Covariates labelled $x_q(j)$, $q=1, \ldots, Q$ (in vector notation: $x(j)$) are recorded at a reference time $t=0$ when no events have yet occurred. In the case of breast cancer, for example, $t=0$ might correspond to the time of the primary operation. Here, the index $j=1, \ldots, J$ refers to the subject number in any order. At times $t_j$, state variables %—an event such as relapse (1) or no event, i.e., censored (0))—are also recorded (follow-up).

Special "covariates" that we will refer to as "treatments" are also assumed to be recorded and denoted by P variables $z_p(j)$, $p=1, \ldots, P$ (vector notation $z(j)$). In this representation, the $z_p$ are not necessarily binary or indicator variables. In an alternative representation for the special case of binary treatments (yes/no), one can code such that for each subject, exactly one of the $z_p$ is unity, the rest being zero. For example, if the same subject can receive two kinds of therapy, this coding would imply four "treatments" (first second, neither or both). If not otherwise stated, we use the former representation, in which more than one component of $z_p(j)$ could be nonzero. A component of $z_p$ could also be any nominal variable, such as an indicator for the population from which the subject was drawn.

We now imagine that each subject represents a random sample drawn from a large pool of subjects with identical covariates x,z. For this pool of subjects, let S(t|x,z) represent the percentage of surviving subjects at time t (here "surviving" refers to the event under consideration, e.g., in the case of relapse it refers to relapse-free survival) with covariates x,z. This can be thought of as the conditional probability for surviving to time t given x and z. It is assumed that $S(\infty|x,z)=0$ and $S(0|x,z)=1$. According to the usual notation, one may define an event density f(t|x,z) and a hazard function $\lambda(t|x,z)$ by $$f(t \mid x, z) \equiv -\frac{dS(x, z)}{dt} \tag{3a}$$

$$\lambda(t \mid x, z) \equiv \frac{f}{S} \tag{3b}$$

These definitions imply that $$\lambda(t \mid x, z) = -\frac{d}{dt}[\log S(t \mid x, z)] \tag{4}$$

Due to treatment strategies, we will observe subject j to have treatment $z_p=1$ with some probability denoted $\phi_p(x(j))$, $p=1, \ldots, P$. The method thus applies to those observational situations in which the decision to give treatment is independent of outcome $\Delta_j$ but could depend on the recorded "covariates" defined as values of explanatory factors. The method of the invention in this embodiment requires an estimate of $\phi_p(x(j))$, which will be referred to as the p-th propensity score (component) of subject j for treatment p. This quantity may be known from guidelines or can be estimated from the data by a suitable statistical procedure since techniques for estimating propensity scores are documented in the scientific literature. "Suitable statistical procedures" include logistic regression (possibly with nonlinear terms), neural network logistic regression, and stratified logistic regression.

The subject data is now augmented by a number not exceeding P of propensity scores. (For example, in a spreadsheet representation of the data, "augmented" data would be defined by appending additional columns to data in which each subject is represented by a row.)

For convenience, a vector X is defined as {x,z} for each subject. This definition amounts to subsuming the treatments in an augmented list of explanatory factors for notational purposes.

The method of the invention considers a hazard model of the form $$\lambda_k(t|X) = \lambda_{k0}(t) h_k(t|X, \phi_1, \phi_2, \ldots, \phi_P) \tag{5}$$

where k denotes the k-th outcome. The hazard is decomposed as $$h_k(t \mid X, \varphi_1, \varphi_2, \ldots, \varphi_P) = \exp\left[\sum_{l=1}^{L} B_l(t) \begin{pmatrix} NN_{kl}(X) - \\ OP_{kl}(\varphi_1, \varphi_2, \ldots, \varphi_P) \end{pmatrix}\right] \tag{6}$$

The neural network (or other learning-capable system) provides the quantities $NN_{kl}(X)$. The quantities $OP_{kl}(\phi_1, \phi_2, \ldots, \phi_P)$ are denoted as the "operating point corrections" for the network outputs, given the propensity scores $\phi_1, \phi_2, \ldots, \phi_P$. The output of the neural network (k,l) is shifted down by an amount $OP_{kl}$. Put differently, in order to produce a given hazard, the network output $NN_{kl}(X)$ must be higher by $OP_{kl}$ than it would need to be for zero operating point.

As described shortly, the invention provides a method for determination of the operating point corrections during training of the neural net or other system.

The $B_i(t)$ are suitable functions of the variable t (such as time). In a preferred embodiment, the $B_i(t)$ are fractional polynomials of integral or half integral positive order. In further specific embodiments, they are (well-known) spline functions. The case of only one $B_0=1$ is known as a proportional hazards model. Deviations from proportional hazards are modelled by including more $B_i$. In this case, the model is said to have "time varying hazards." The time dependence is explicitly contained in the $B_i(t)$.

In a preferred embodiment, the operating point corrections are decomposed by $$OP_{kl}(\phi_1, \phi_2, \ldots, \phi_P) = OP_{kl1}(\phi_1) + OP_{kl2}(\phi_2) + \ldots + OP_{klP}(\phi_P) \quad (7)$$

By Eqs. (5) and (6), this decomposition corresponds to a multiplicative effect on the hazard.

In a preferred embodiment of the invention, the propensity scores for each component are separately ranked. A number N_p of categories are defined in terms of increasing rank. These categories are designated "strata" for the purposes of the method. In a specific embodiment, roughly equal numbers of subjects are assigned to each category of each component. In another specific embodiment, the number N_p of strata and the assignment of subjects is defined for each p such that a an appropriate statistical test such as a Chi-squared test yields no significant differences between treated and untreated subjects in each component at each stratum at a specified level of significance such as 99%, 95% or one standard deviation.

Based on the propensity scores, each subject is initially assigned to a stratum for each treatment as defined above.

As explained above, additional strata with respect to any other nominal variable(s) that could affect the hazard can be incorporated into this scheme by increasing P. For example, in pooled subject data from different study centers, strata could correspond to centers. The property of belonging to the population of a center may be viewed for the purposes of the invention as a kind of "treatment".

The representation of the operating point corrections is now easily accomplished by look-up tables. For each k and l, the p-th term in (7) is represented as a vector of dimension N_p.

Specific embodiments are outlined below.

The method of the invention provides a procedure for determining the operating point corrections. Recalling the explanation following Eq. 2b for the neural outputs, one sees that these are defined to make the median output vanish. In a preferred embodiment of the invention, the separate addends $OP_{klp}(\phi_p)$ of the operating point corrections $OP_{kl}(\phi_1, \phi_2, \ldots, \phi_P)$ are defined such that the median of all signals corrected according to Eq. (7) in each stratum of treatment p vanishes.

The method also provides a method for computing an adjusted score that takes into account possible differences in the distributions of explanatory factors in going from one stratum to another. This is accomplished as explained in detail below by an application allowing specification of reference levels or values of each explanatory parameter.

Optimization

In a broad class of applications, an objective function of the form $$L(\mu; \{X_j, t_j, \delta_{jk}\}) = \prod_{j=1}^{n} F\left( \begin{array}{c} [f_{NN(k,X_j)}(t_j)]; [S_{NN(k,X_j)}(t_j)]; \\ k = 1, \ldots, K \end{array} \right) \quad (8)$$

is to be optimized. The notation is intended to express the idea that the function F may depend in some as yet unspecified manner on survival and failure probabilities. This dependence is problem-specific but derivable from a logical model of the occurrence of the various failure modes for the outcomes.

The parameters denoted by $\mu$ are the survival scales $\lambda_{0k}$, the weights of the neural net, and a matrix of operating points for the neural net strata.

A preferred class of objective functions of the form (7) are known as likelihood functions. For the example, the form $$L(\mu; \{X_j, t_j, \delta_{jk}\}) = \prod_{j=1}^{n} \prod_{k=1}^{K} [f_{NN(k,X_j)}(t_j)]^{\varepsilon_{jk}} [S_{NN(k,X_j)}(t_j)]^{\psi_{jk}} \quad (9)$$

is chosen.

The two arguments $f_{NN(k,X)}, S_{NN(k,X)}$ (subscripts and vector notation suppressed) are uniquely determined provided the neural net or learning-capable model provides the required output. This is always the case in the specified example. The functional dependence of the model is denoted symbolically by variable parameters $\mu$.

The embodiment (9) is capable of describing competing risks. Here, $\varepsilon_{jk}$ and $\psi_{jk}$ are determined from $\delta_{jk}$ by their logical relationship, where $\delta_{jk}=1$, if subject j suffers a recorded failure of type k at time $t_j$ and otherwise $\delta_{jk}=0$. Censored data correspond to subjects who have suffered no recorded failure, so that $\delta_{jk}=0$ for all k=1, 2, 3, . . . .

A nontrivial example illustrating the procedure for determining $\varepsilon_{jk}$ and $\psi_{jk}$ from the logical relationships is as follows: In the case of the disease breast cancer, three outcomes of interest could be bone metastasis (B, for "bone", k=1), other distant metastasis (D for "distant", k=2), or loco-regional (L for "local", k=3). Simultaneous occurrence of all three outcomes at observation month t is possible. However, in the example suppose (for clinical, therapeutic, or data-technical reasons) the follow-up observation in month t is classified according to the following logic:

bone metastasis (yes/no) ?

If yes, then $\varepsilon_{j1}=1\varepsilon_{j2}=0\varepsilon_{j3}=0\psi_{j1}=0\psi_{j2}=0\psi_{j3}=0$ If no: other distant metastasis (yes/no) ?

If yes, then $\varepsilon_{j1}=0\varepsilon_{j2}=1\varepsilon_{j3}=0\psi_{j1}=1\omega_{j2}=0\psi_{j3}=0$ If no: loco-regional (yes/no)

If yes, then $\varepsilon_{j1}=0\varepsilon_{j2}=0\varepsilon_{j3}=1\psi_{j1}=1\omega_{j2}=1\psi_{j3}=0$ If no, then $\varepsilon_{j1}=0\varepsilon_{j2}=0\varepsilon_{j3}=0\psi_{j1}=1\psi_{j2}=1\omega_{j3}=1$ In other words, in this rule, the observation of bone metastasis is assigned priority so that the other outcomes do not count even if they occur at t. Other examples of the recording priorities can be handled similarly.

In a preferred embodiment, the time integrals that arise in the solution of Eqs. 2-6 are solved by the standard method of Romberg Integration. This method permits the utilization of arbitrary time variation in the functions $B_i(t)$.

At time t, let S(t) be the expectation value of the fraction of subjects having had no failure of any type k=1, ..., K. In the specified example, this quantity is given by the product of the individual probabilities:

$$S(t) = \prod_{k=1}^{K} S_k(t). \tag{10}$$

The neural network operating point represents the median response among all subjects. For each subject, the invention embodiment discussed above provides a method for assigning a response typical of subjects with similar propensity scores by means of the median in the stratum to which the subject is assigned on the basis of the appropriate propensity score. In this embodiment, the neural net output then represents the log hazard of this subject compared to subjects with similar propensity scores or an analogous quantity as required.

The method of the invention is also applicable if the "response of subjects with similar propensity scores" is assigned by an alternative method, such as a (possibly) weighted average of responses of subjects with nearby propensity scores for the treatment in question.

Application to Risk Assessment for New Subjects

For application to a new subject, one alternative provided by the invention is to supply a propensity score according to the propensity model of the original data used to train the learning-capable system. We then know the probability that the subject would have been treated, if she had been in the original data set. This number tells us the proper comparison sample and thus, through the look-up table, the operating point of the neural net The original scores defined by the neural network for a subject in the training set refer to an operating point which is defined according to Eq. (7). In one embodiment, the corrections are determined as the median output of all subjects in the corresponding stratum of treatment p, p=1, 2, ..., P. The assignment of a subject to treatment is closer to an ideal random draw within a stratum with probability corresponding to the average probability of treatment p in the stratum. Hence, the neural network learns the risk compared to other subjects that have nearly the same probability of receiving treatment p. The probability model is designed to decouple the part of the influence of explanatory factors x on hazard that is independent of the probability of being treated ("direct influence" in what follows) from their influence on hazard due to their influence on the probability of treatment(s) ("indirect influence" in what follows). Their direct influence as well as the influence of treatment is associated with the term $NN_{kl}(X)$ in Eq. 6, whereas their indirect influence is represented by $OP_{kl}(\phi_1, \phi_2, \ldots \phi_P)$, where we note that each of the propensity scores $\phi_p$ depends on the x variables as well. (Here we recall that the notation X refers to all explanatory variables including treatments, whereas x refers to those factors that are not treatments.) The direct influence is an intrinsic property of the disease, whereas the indirect influence is an artifact of treatment policies and is not generalizable to a situation with a different treatment policy.

The probability model of Eqs. 3-11 as applied here supplies hazard scores with respect to two references:

1. the median score of the stratum to which a subject with factors x would have been assigned in the observed study
2. the median over all subjects of the observed study It is often desirable to apply the trained system to the prediction of outcome for a new subject in a new context
  for whom treatment assignment is either not yet determined (e.g., in decision support), or
  whose treatment assignment could be performed according to rules differing substantially from those of the observed study.

To facilitate this application, the invention provides for the construction of a third reference that is advantageous in assessing a new subject: this is accomplished by introducing an idealized reference subject with specified values $X_0$ of all explanatory risk factors X (i.e., including treatments). For example, in primary breast cancer, it is customary to refer risks associated with positive affected lymph nodes to the risk of a node-negative patient, rather than to the risk of a patient with the median number of affected nodes. Furthermore, since the options available in decision support are usually "treatment" vs. "no treatment" it would often be useful to define the reference z as "no treatment", even if a subject in the original study with factors $X_0$ would have been treated with high probability. Finally, such a procedure is especially advantageous if a reference subject can be found such that the (time-varying) hazard of the reference subject can be estimated from available data in the population under consideration. This is often possible if the "reference subject" belongs to a group with high frequency.

Formally, the relative hazard $H(t, X, X_0)$ of a subject with factors X is now defined with respect to the hazard of a subject with factors $X_0$ by $$H_k(t, X, X_0) = \exp\left[\sum_{l=1}^{L} B_l(t)(NN_{kl}(X) - NN_{kl}(X_0))\right] \tag{11}$$

Notice that the operating point corrections do not appear in this formula, since according to this definition the hazard of both the subject with factors X and of the reference subject with factors $X_0$ are referred to the median of the same stratum (the result being the same as if both were referred to the median of the original study).

The reasoning behind referring both the true and reference subject to the same stratum s is as follows: One imagines the stratum s as if it were a sample of an ideal randomized study on a large population with treatment probability corresponding to the mean treatment probability in the stratum. The stratum population thus represents a sub-population of the total population of the ideal randomized study, which includes in particular the reference subject.

Defining $$\Delta NN_{kl}(X, X_0) = NN_{kl}(X) - NN_{kl}(X_0) \tag{12}$$

this definition has the desired property that one can recover the hazard in Eq. (6) from the reference hazard $\lambda_k(t|X_0)$ and the relative hazard $H(t, X, X_0)$ using $$\lambda_k(t|X) = H_k(t|X, X_0) \times \lambda_k(t|X_0) \tag{13}$$

In other words, because the risk scores appear logarithmically in the probability model, this reference shift corresponds to a multiplicative shift in the hazard. From this knowledge, it would be possible to estimate survival curves S(t) for a subject with factors x with any combinations of proposed treatments including no treatment. The estimates of treatment effects for a subject with a given set of explanatory factors x reflect the learning of a neural network within strata of nearly constant treatment probability. Assuming that reference subject has been chosen such that the estimated survival probability function (and hence the hazard) of the reference subject—for whom all factors $X_0$ including treatment are specified—should not depend on the percentage of subjects treated in the idealized study, then the relative hazard in Eq. (12) provides an estimate of the hazard ratio that would have been obtained from the ideal randomized study.

In a preferred embodiment, the process of obtaining output from a trained neural network or other learning-capable system for a new subject is implemented as an application that could be executed for example via an internet browser user interface. The subject's characteristics (including both information used to characterize the population to which the subject belongs and "individual" factors) may be entered into a standardized template. In one embodiment, outcome assessment is provided in the form of one or more scores with a suitable standardized or objectifiable interpretation.

Example

The procedures are specified in an example as follows:

The method of the invention is illustrated by a simulated study with explanatory x variables xlypo, xer, xpr, xage, xtum, xupa, xpai1 and a z variable, the treatment ct.

The probability model for generating the explanatory variables was the same as that given in Tables 1a and 1b.

The target natural median survival (that is, in the absence of treatment) was taken to be 48 months and the study was modelled as censored with censoring times uniformly distributed between 70 and 100 months. Due to treatment, the true median survival was 81 months.

The interpretation of the last line and the last column of Table 3 is simply that the total effect of treatment was modelled as a reduction $\Delta \ln(hr)$ of the log hazard given by the formula $$\Delta \ln(hr) = -1.00 * [1 + 0.3 * (xupa\text{-median}(upa)) + 0.3 * (xpai1\text{-median}(pai1))]$$

In order to demonstrate a typical situation in outcomes research, the treatment was not applied entirely randomly, but such that the probability P of receiving ct depended strongly on the level of the variable xlypo according to $$P = \exp(\psi)/(1 + \exp(\psi))$$

with $$\psi = 1.5 * (xlypo\text{-median}(xlypo))$$

TABLE 3

| Factor number | name | Log hazard | Log treatment interaction |
| --- | --- | --- | --- |
| 1 | xlypo | 2.00 | 0.00 |
| 2 | xer | 0.00 | 0.00 |
| 3 | xpr | 0.00 | 0.00 |
| 4 | xage | −1.00 | 0.00 |
| 5 | xtum | 1.00 | 0.00 |
| 6 | xupa | 0.75 | 0.30 |
| 7 | xpai1 | 0.75 | 0.30 |
| 8 | ct | −1.00 | x |

Of the 2500 subjects, this treatment policy resulted in 1246 treated subjects and 1254 intreated subjects. A propensity scoring model of this treatment policy was generated by ordinary logistic regression, and the scores φ were recorded with the remaining explanatory variables for each subject A stratified neural network as described above was trained with 50% randomly chosen subjects. In this example, K=1 (one outcome), L=1 (one time function) and P=1 (one treatment). Hence, there is only one output node to correct (k=1 and l=1) and one treatment (p=1), so that there is exactly one set of operating point corrections. 10 strata of approximately equal size were identified and labelled by an index s. Table 4 summarizes the stratum definitions (lower boundary in φ(s)) and the operating point corrections OP(φ(s)) resulting from the trained neural net.

TABLE 4

| stratum lower boundary of treatment probability | | operating point correction |
| --- | --- | --- |
| s | φ(s) | OP(φ(s)) |
| s = 1 | 0.376 | −0.079 |
| s = 2 | 0.414 | −0.076 |
| s = 3 | 0.442 | −0.107 |
| s = 4 | 0.471 | −0.028 |
| s = 5 | 0.492 | 0.039 |
| s = 6 | 0.525 | 0.025 |
| s = 7 | 0.546 | 0.012 |
| s = 8 | 0.578 | 0.105 |
| s = 9 | 0.623 | 0.003 |
| s = 10 | 0.777 | 0.129 |

Figure 5:
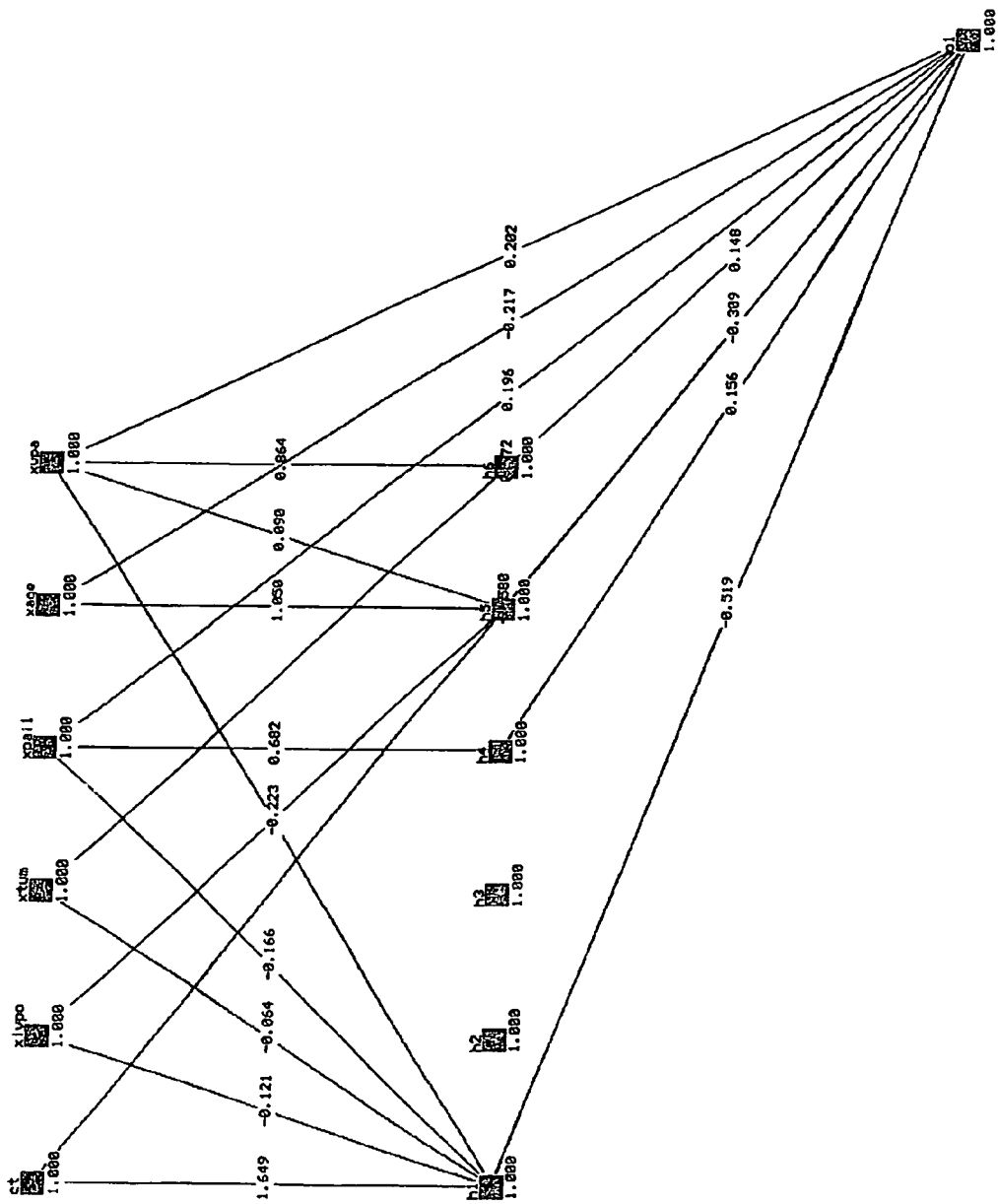
FIG. 5 shows a schematic diagram illustrating an example of a trained neural network.

FIG. 5 illustrates the resulting trained neural network.

In the example, a reference subject was chosen to have factors $X_0$ (see preceding section) as given by Table 5.

The adjusted score $\Delta NN_{kl}(X, X_0) = NN_{kl}(X) - NN_{kl}(X_0)$ was constructed for each subject using $X_0$ from Table 5 and compared with the "true" logarithmic hazard generated from the risk model of Table 3 for both the training set and for a generalization set not used for training the neural network. The correlation of the true score with the adjusted score was 0.783 in both cases. Hence, there was no degradation going from the training set to the generalization set.

TABLE 5

| $X_0$ | reference value |
| --- | --- |
| ct | 0 |
| xlypo | 0.00 |
| xtum | 0.00 |
| xpai1 | 0.49 |
| xage | 0.50 |
| xupa | 0.49 |

Figure 6:
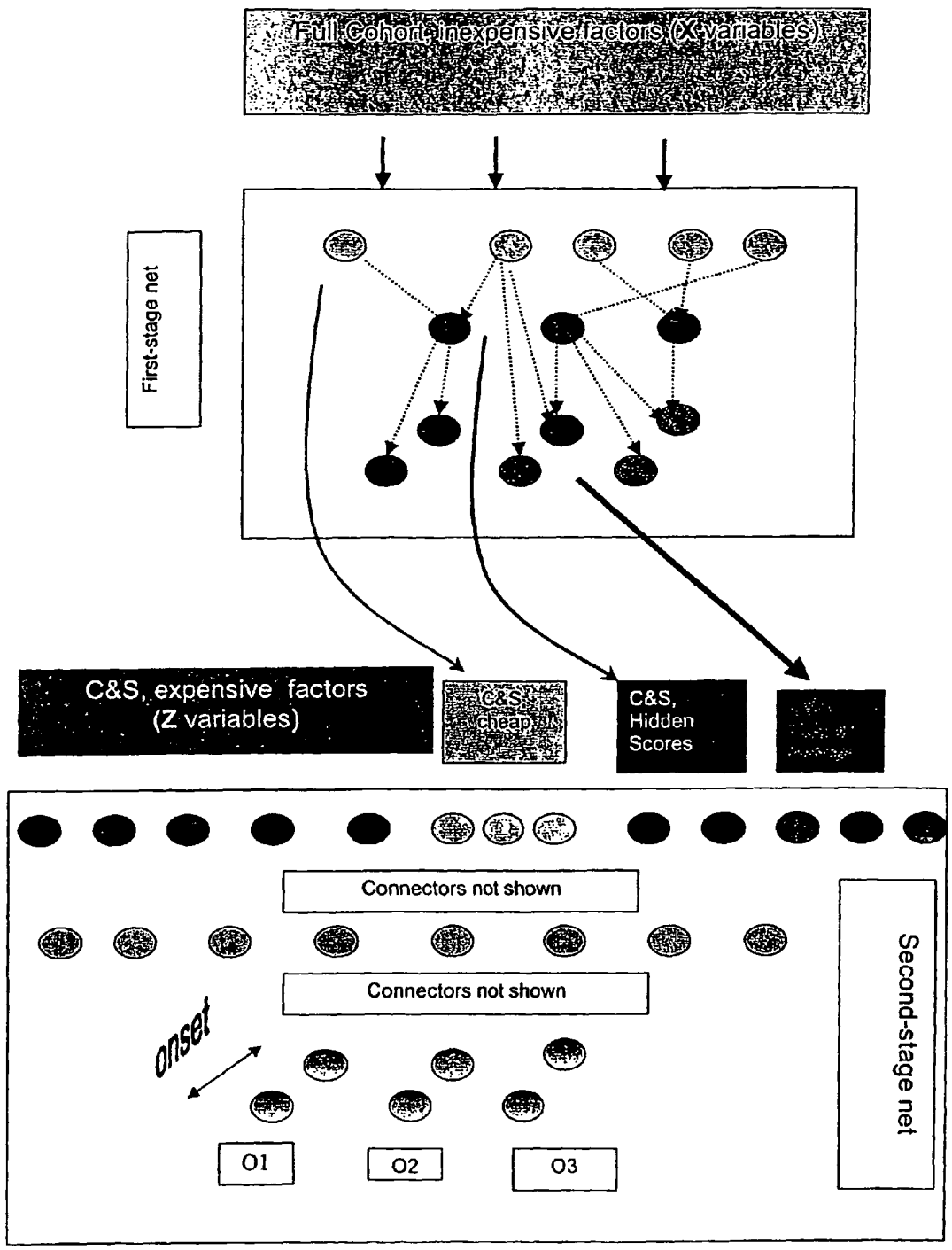
FIG. 6 shows a schematic diagram illustrating a multi-stage neural network with three competing risks.

Specification of the Invention for Special or Restricted Data Acquisition Design: Multi-Stage Neural Networks The present embodiment addresses the deficiencies of the state of the art by a multi-stage representation of outcome hazard and a multi-stage training scheme for the learning capable system. The invention embodiment is illustrated first in FIG. 6 for the case of a multi-stage neural network with three competing risks r=1, 2, 3 corresponding to output scores O1, O2, and O3. (In this picture, there is no distinction yet among the factors $Z_r$, i.e., the picture describes a situation in which all Z are measured in cases involving any of the three outputs.)

First Stage:

Use X covariates to train a learning capable system, here idealized as a neural network, on a sample of all subjects. This network provides output scores for all outcomes based on the information in the X variables including if required additional scores related to time varying effects. In the case of a neural network with a hidden layer, the final activations of any remaining "hidden" nodes (see Eq. 2a) may also be recorded for each subject. Although it is customary not to record hidden node scores in neural network applications, because they are not used in the objective function to determine the fitness of a configuration, they are readily available to the application and are important to this embodiment of the invention. Hidden node activations may always be interpreted as auxiliary scores that are available for further processing.

In another embodiment, hidden nodes are not used, but the output scores of the first stage are combined using multiple instances of the learning-capable system as described earlier. Doing so would allow combination of the invention embodiment for (sporadic) missing data with the present scheme of incomplete data by design.

Second Stage:

Use X and Z variables, together with all scores of first stage—including, in a preferred embodiment, hidden node scores—as input nodes to a second neural network. The second network is trained on the C&S sub-cohorts, defined above. In addition, the second neural network would be subject to some special constraints:

1. The scores are to be normalized appropriately to reflect the incidence of cases in the whole cohort, not just the fraction of cases in the C&S subset used for second-stage training (cases and sub-cohort.) This is accomplished in a preferred embodiment by setting the operating point of the second stage output layer such that the median score is not zero, as was done for the original collective, but rather equal to the median score in a corresponding subgroup of the original collective from the first stage.
2. In an embodiment appropriate for the case in which first-stage factors (X) are easier or cheaper to obtain than the others, one may exempt from pruning some or all of those input nodes associated with the scores obtained from the first-stage neural network. In the first-stage net, any connector can be pruned, and if all the connectors to an input node are pruned, then that input node is effectively irrelevant and gets pruned automatically.

Constraint 1 incorporates the prior knowledge of incidence obtained from a representative sample into the second-stage training scheme.

The rationale of point 2 is that if the X information used to train the first network is cheaper to get, there could be a preference for using only that subset of the expensive information in the second net that is indispensable for the overall performance. By forcing the information from the first-stage scores to stay in the second network, the costs of measurement are reduced by using the information provided by inexpensive factors wherever possible. several desirable ends are accomplished. Again, several instances of a learning-capable system can be combined in the second stage as well.

The first stage already is a full-fledged individualized risk-assessment tool. By comparing risk assessment/classification performance delivered by the first stage alone with that of the combined first & second stages, the invention provides a method for characterising the gain in performance provided by making more expensive measurements compared to making only cheap measurements. This capability could be utilized in the framework of a cost-benefit analysis.

Extension of Multi-Stage Neural Network Scheme for Competing Risks when Factors Measured depend on particular outcome If multiple, possibly competing outcomes are present, there could be prior information or evidence allowing one to exclude consideration of the influence of a subset of factors $Z_r$ on an particular endpoint. It then could be advantageous in order to reduce cost, manpower, time and to preserve samples to have a learning-capable system capable of modelling this situation. The invention provides for a solution to this situation as well. That is, in addition to the embodiment for a multi-stage neural network in a situation in which all aforementioned factors $Z_r$ are measured in cases involving any of the multiple outputs, the invention also provides for an embodiment in which the choice of factors $Z_r$ to be measured depends on the outcome $O_r$.

We have $C_r$ cases with outcome $O_r$, r=1, 2, 3, . . . R. The total number of subjects C with some outcome could be less than the sum of the $C_r$ if multiple outcomes are possible. In a competing-risk model, multiple outcomes are excluded by definition, and strict equality would hold.

Let X be the covariates measured for all subjects as before. We define measurement clusters $Z_r$ as the set of characteristics measured on the $C_r$ cases and on a subset of $S_r$ other subjects. Note that those characteristics relevant to more than one outcome are represented in both measurement clusters $Z_r$.

The first stage is identical to the previously described scheme, since all cheap markers are measured on all subjects.

Figure 7:
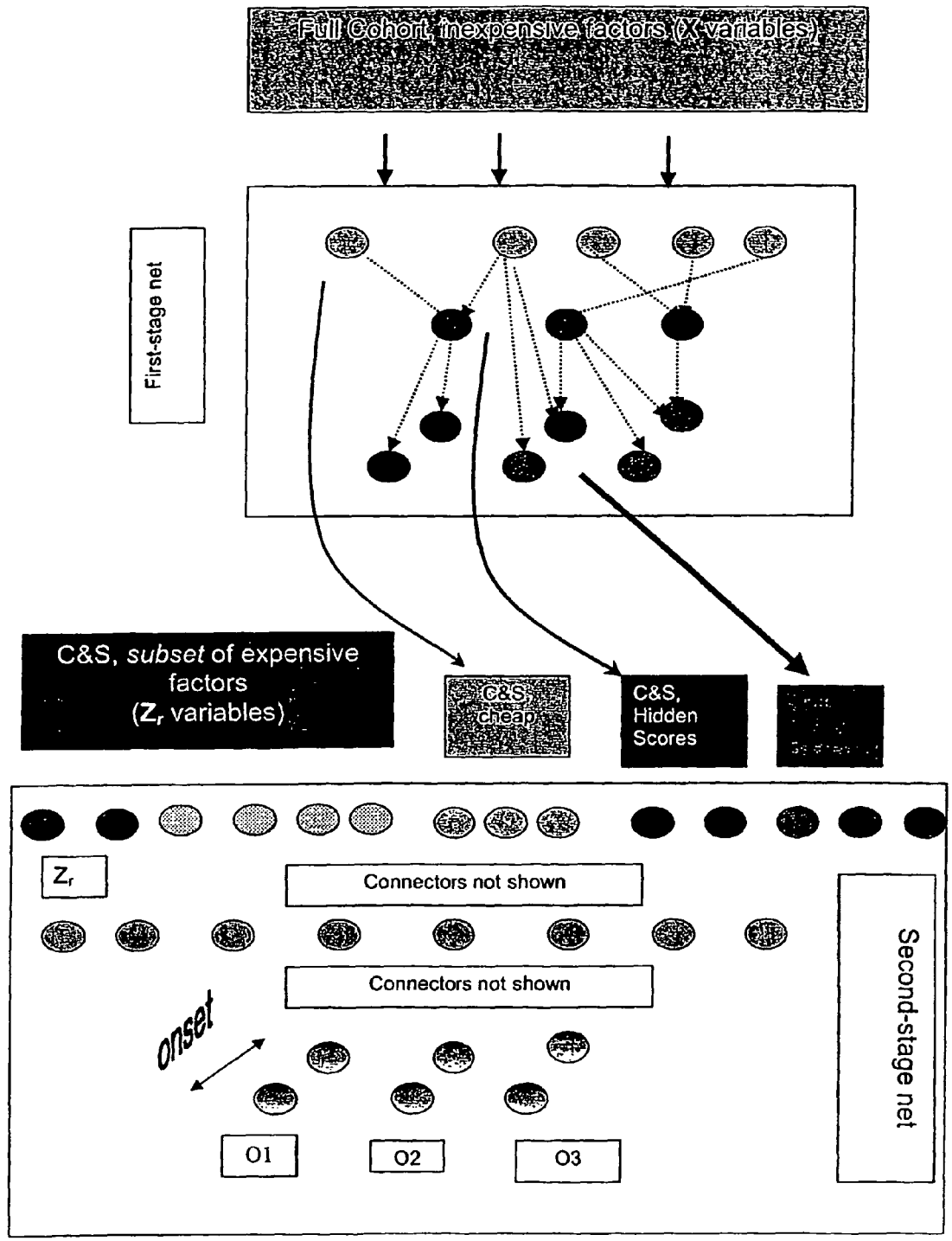
FIG. 7 shows a schematic diagram illustrating another multi-stage neural network.

The proposed solution to the measurement problem for "expensive markers" is to introduce R "incarnations" of the second-stage neural net. One such incarnation is shown for the case R=3 in FIG. 7, which resembles the diagram of the previous two-stage neural net design except for the use of the measurement cluster $Z_r$: The measurement strategy described above is represented schematically in the figure by supposing that only the two filled nodes on the left are measured for the endpoint r.

There will be R incarnations of the second stage, one for each $Z_r$ (i.e., one for each measurement cluster). As mentioned above, the "same" filled circle (measurement) could be present in more than one incarnation, if it is present in the corresponding measurement clusters.

Example

The method of multi-stage learning-capable systems for a special or restricted data acquisition design is now illustrated by an example with a multi-stage neural network. We begin with a simulated study of 9 factors, named xlypo, xer, xpr, xage, xtum, xupa, xpai1, ct, and ht, of which only the first 5 were assumed to be measured in all subjects. A total of 15000 subjects were generated for the simulated study. The probability model for the first seven simulated explanatory factors xlypo, xer, xpr, xage, xtum, xupa, xpai1 was assumed to be as in Tables 1a and 1b. The two remaining factors are binary variables labelled "ct" and "ht" as in previous examples. However, here these two factors are not considered as "treatments" but the interpretation is simply that of binary-valued subject characteristics. In the example, neither binary factor is correlated with any other factor. The frequency of "ht" is 1508/15000, and the frequency of "ct" is 4085/15000.

The "true" disease as simulated in this example had one endpoint/outcome associated with "failure". The "true" risks were generated according to the nonlinear risk model of Table 6. Of the 7500 subjects used for training, 1311 had failures. The survival times were generated as earlier using exponential deviates taking the hazard into account with median survival 102 months. The outcomes were censored as before at random times uniformly distributed between 11 and 15 months.

Figure 8:
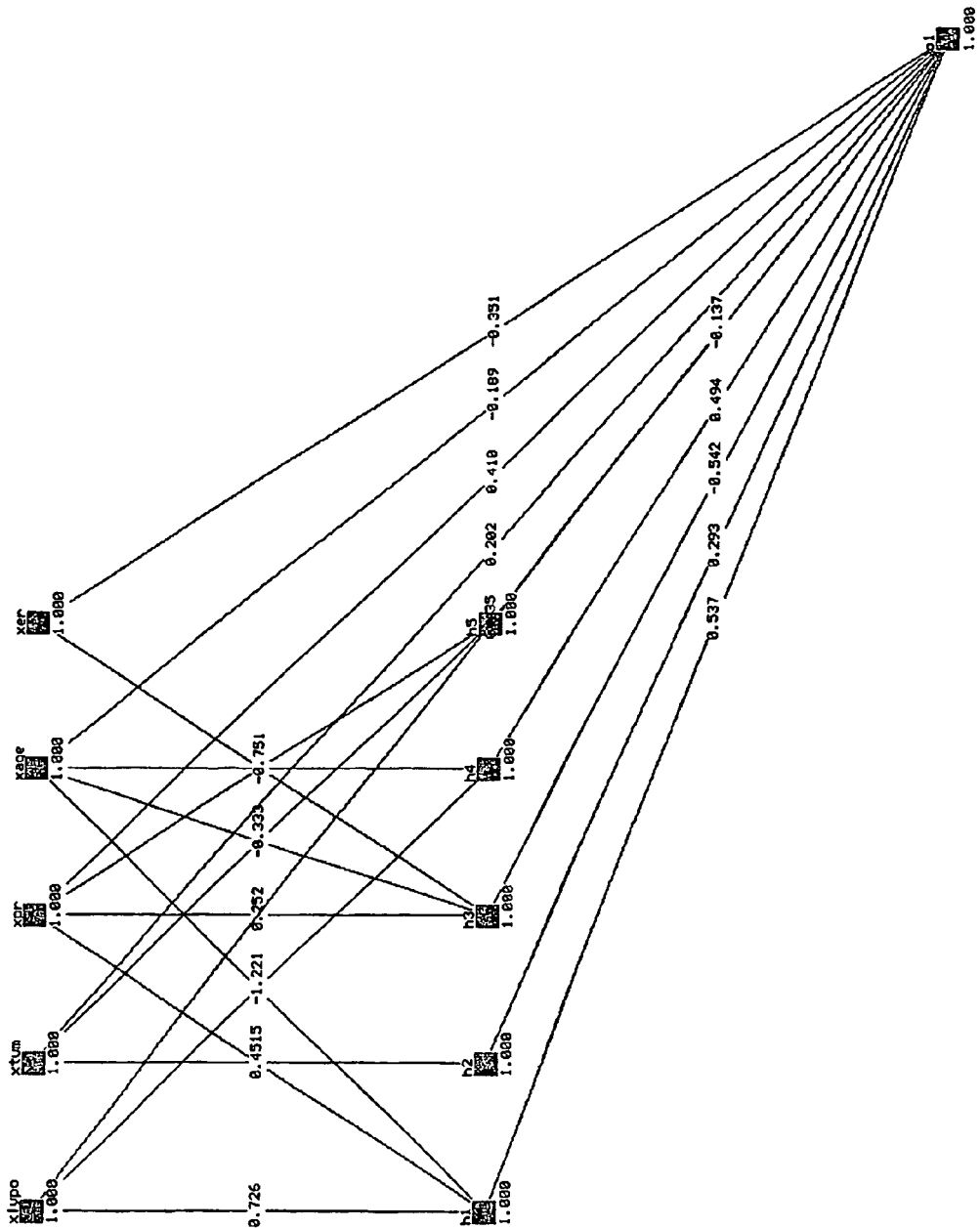
FIG. 8 shows a schematic diagram illustrating a first-stage neural network.
Figure 9:
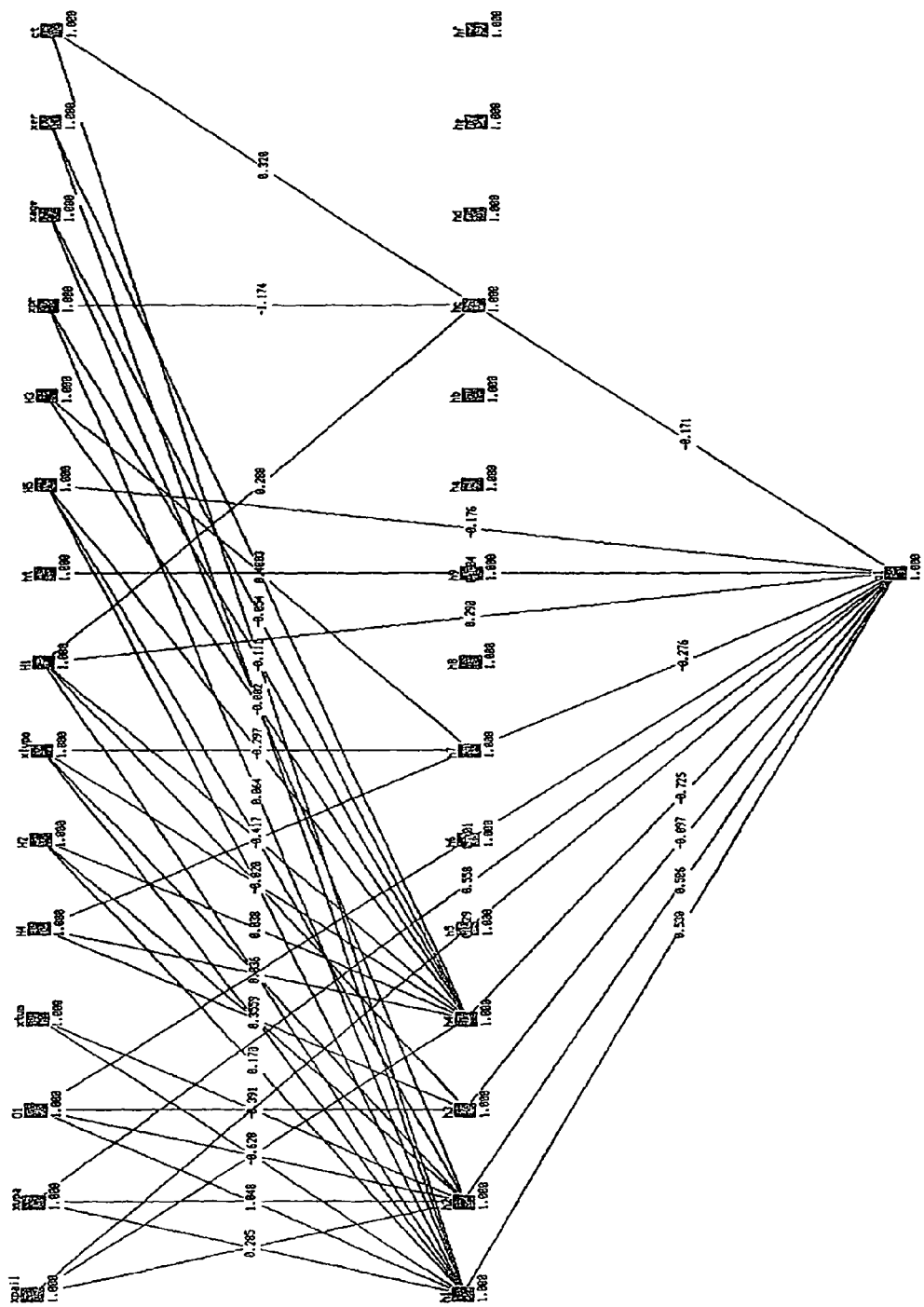
FIG. 9 shows a schematic diagram illustrating a second-stage neural network.

For the first five factors that were measured in all simulated subjects (xlypo, xer, xpr, xage, and xtum), a first-stage neural network was trained on 7500 of the 15000 subjects, with these factors as input nodes. The resulting first-stage network is illustrated in FIG. 8.

Note that all five of the hidden nodes remain unpruned in this example. For each subject, the output o1 and the unpruned (in this case all) hidden node scores were recorded next to the original explanatory data (and relabelled O1, H1 to H5 to avoid confusion with the second-stage nodes).

The number of input nodes for the second-stage network is thus 15 (9 inputs, 5 hidden scores from stage 1, 1 output score from stage 1). For the second-stage neural network, a random set S of 1326 controls was generated from the first-stage training set, combined with the 1311 cases (C), and used to train the network. The median score on this set was computed (median score=0.1) and used as the operating point for the second stage network. That is, the median score of the patients used to train the second-stage network is by construction the same as the median first-stage score of the same group.

TABLE 6

| factor | name | log hazard |
|---|---|---|
| 1 | xlypo | 2.00 |
| 2 | xer | 1.00 |
| 3 | xpr | 1.00 |
| 4 | xage | −1.00 |
| 5 | xtum | 1.00 |
| 6 | xupa | 4.00 |
| 7 | xpai1 | 5.00 |
| 8 | ct | 1.00 |
| 9 | ht | 0.50 |
|  | Interaction xupa and ct | 3.00 |
|  | Interaction xpai1 and ct | 3.00 |
|  | Interaction xlypo and ct | 1.00 |

As it turned out, all of the first-stage nodes remained significant in the second-stage net. This need not always be the case.

As a check, receiver operating characteristic curves with respect to events (I/O) were constructed on training data of the second-stage neural net for
1. the "true" risk (calculated using Table 6),
2. the first-stage neural net output scores (O1), and
3. the second-stage neural net score o1

The resulting AUC-values (area under the curve) were given by

| score | AUC (training) |
|---|---|
| true risk | .894 |
| first stage | .641 |
| second stage | .870 |

The correlation coefficient between the true risk and the second-stage score is 0.875 in this example.

In a real application the true nature of risk interactions is generally unknown and could be much more complex than the quadratic interactions of Table 6.

Specification of the Invention for Incomplete Explanatory Data in Learning Capable Systems: Multiple Imputation The invention provides a method designated in what follows as "multiple imputation" for addressing the problem of incomplete explanatory data for the use of learning capable systems to relate subject characteristics to subject outcomes. The problem is solved by training and recording not just one, but a library of trained learning capable systems such as neural networks, where the "library" is defined as follows: Each member of the library is an algorithm for producing one or more desired scores or other quantifying measures of outcome based on the explanatory characteristics. The uncertainty associated with the imputation of missing data is reflected in the variations among the scores from different members of the library. The method of the invention may furthermore be used or combined with the other embodiments of the invention.

The multiple imputation method comprises a procedure for generating multiple complete data instances (collectives), each of which is to be used for training at least one instance of a learning capable system. The collectives all agree on the available (i.e., not missing) data entries. The imputations of missing data for each subject have an element of randomness that takes into account what is known or can be inferred from a model of the distribution of the missing information conditional on the available information. Hence, different instances of the imputed data will differ, and for each subject with imputed values, the differences among instances reflect the uncertainty in imputation conditioned on what is known. Due to the element of randomness, the relationships between explanatory factors and outcome inferred by the learning-capable system will exhibit random variations as well, and these are reflected in the variations among the scores from the aforementioned library.

If the training procedure for said learning-capable system also has an element of randomness, such as is usually the case with neural networks, then multiple instances of training for each instance of imputation can be included in the library, in a particular embodiment of the invention.

The invention improves the state of the art in training of learning-capable systems to represent the relation of outcome to characteristics of subjects in several specific respects, including the following:

compared to listwise deletion:
The invention reduces or removes a source of bias that would otherwise have arisen with listwise deletion, for example, if "missingness" (probability to have one or more factors missing) in subjects is related in any way to factors or outcome.
Loss of power (number of subjects) is avoided; in the extreme case, sometimes a factor that would have provoked deletion of a subject turns out to be irrelevant upon training. Subjects that were deleted on the basis of such irrelevant factors would be lost to the analysis even though the factors could, in retrospect, have been ignored.
compared to factor deletion:
The invention allows retention of explanatory factors even if some subjects have missing data in these factors, so that the explanatory power of the model does not need to be reduced as it would in factor deletion.
compared to univariate imputation (e.g., mean imputation):
The invention avoids a severe inaccuracy and a source of bias associated with the state of the art
compared to EM:
The invention provides a range of imputed values whose distribution reflects what is known The invention provides a measure of the uncertainty of the outcomes produced by the learning capable system in the presence of incomplete data. For example, the variance of the outcome score instances is a measure of the uncertainty associated with multiple imputation. The invention is applicable to the training of any learning capable system that requires or prefers complete data in the explanatory variables and produces outcome scores depending on explanatory variables.

The library solution to the problem of characterizing uncertainty is particularly appropriate for use with learning-capable systems such as neural networks whose realizations can exhibit variations in the topology and parameters that represent the risk structure—even when trained with complete data. Note that in such cases, the (multivariate) distribution of system parameters may be inherently complex and difficult to model. Nonetheless, even in such cases the library will provide a realization of the distribution of scores for each subject. The extra variance associated with multiple imputation may thus be treated in a manner qualitatively similar to that associated with multiple instances of the trained system even with complete data. In the case of a patient with missing data, the uncertainties can of course be quantitatively greater.

The invention furthermore provides a solution to the problem of obtaining an outcome estimate for a new subject with incomplete information, for whom—as stated above—deletion is not an option. In this case, multiple imputations of the missing values for the new subject may be generated by the method to be described below.

Summary of Invention Embodiment "Multiple Imputation for Learning-Capable Systems"

According to the method of this embodiment of the invention, multiple instances of complete "imputed" data sets are to be generated for training multiple instances of a learning-capable system. In each complete data set, the imputed data comprises a complete set of values of explanatory values for each subject. Available (not missing) values are simply repeated in each imputed data set, whereas multiple imputations of missing values are to be generated as realizations of a distribution modelled by taking into account the available explanatory factors of the subject according to a statistical model of the distribution of said explanatory factors. The parameters of the statistical model are estimated at the same time as described shortly.

Description of the Algorithm

The invention is described for an embodiment in which incomplete (missing) values occur in metric explanatory variables or in ordinal variables that may be treated as if they were metric. In this embodiment, the distributions of all variables are modelled as Normal. To achieve this requirement, the invention provides a pre-processing step if required.

Pre-Processing Step (If Required)

In a particular embodiment, explanatory variables whose univariate distributions differ significantly from a Normal distribution (when the complete values are considered) are first transformed in a preliminary pre-processing step by a univariate monotonic transformation to new variables that are approximately described by a Normal distribution. For a continuous metric variable, one could easily construct and tabulate such a transformation, for example by 1. first constructing fractional ranks of the complete portion of the data for the variable in question and
2. then using the inverse error function, truncated at $\pm A$, where A is a range of standard deviations, over which imputations are required The level of truncation A is defined in a preferred embodiment to be any value such that $A<A0$ such that $\exp(-A0^2/2)=1/N$ for sample size N and $A>1.96$ (for confidence interval 95%).

If it is impossible to meet both conditions, then the first condition is to be dropped.

The method of the invention is highly insensitive to the precise value of A within these ranges.

By constructing a table of values and using a simple interpolation between values, either or both of the transformation steps could then be inverted to obtain original variables or fractional ranks for further processing as desired.

If, for any subject j and any explanatory variable $x_k(j)$ a value within the allowed range is not available (this includes the case of values that are recorded but inadmissible), the explanatory variable $X_k(j)$ is coded as "missing," otherwise "not missing". The explanatory data is read into memory.

Imputation Algorithm

The algorithm now proceeds through an initialization stage, an iterative estimation stage, an iterative imputation stage, and an output stage.

Initialization stage: The explanatory factors to be considered are specified by the user and recorded. This set could comprise a subset of the available factors. The number of required imputations are specified by the user and recorded. A convergence condition for the estimation stage is recorded (fractional change of objective function less than specified limit such as machine precision) along with a maximum number of allowed iterations and/or maximum iteration cpu time. [Usually, in a typical collective with 5000 subjects, a stable numerical estimate is quickly reached so that cpu time does not play a role, but one embodiment of the invention does provide for a maximum computational time to cover the case of very large data sets (millions of entries).]

Estimation Stage:

1. Ordinary means of the univariate distributions are first determined from the subset of complete data for each explanatory factor and substituted as initial values for the missing values.

2. An estimation procedure related to expectation maximization is carried out. The following steps are iterated until desired convergence conditions are fulfilled or until a maximum number of iterations or a maximum time limit are exceeded. In the example, convergence was quite rapid.

A. The covariance matrix of all data is updated and the current value is recorded.

B. The performance measure (likelihood function) is updated and the current value is recorded.

C. For subjects with missing data:

C1. The multivariate conditional probability distribution of those factors with missing values [$X_{k1}(j)$, $X_{k2}(j)$, ... ] for the subject j is obtained from the known (non-missing) values of factors for subject j and the current estimate of the multivariate distribution of all factors.

C2. The conditional expectation value of each missing value is obtained from this conditional probability distribution.

C3. The missing values are updated, i.e., set equal to the corresponding expectation values obtained using the reduced covariance matrix. The reduced covariance matrix can be obtained from the full covariance matrix and the known factors by well known formulae. Said expectation values are of course not the simple means of the univariate distributions, because they also include information about correlations. For example, if two variables $X_1$ and $X_2$ are, say, positively correlated and $X_1$ is known to have a value above the mean, then the probability for $X_2$ (supposed missing) to have a value above its mean is increased.

Imputation Stage:

The imputation stage is repeated at least as many times as imputations required. The invention provides for a "Markov Chain Monte-Carlo" simulation (MCMC). Examples of MCMC algorithms known in the art include the so-called "Metropolis Algorithm" and the "Gibbs Sampler". Several steps are similar to those of the estimation stage. However, the generation of missing values is different from the procedure during the estimation stage (shown in italics).

D. The covariance matrix of all data is updated and the current value is recorded.

E. The performance measure (likelihood function) is updated and the current value is recorded.

F. For subjects with missing data:
  F1. The multivariate conditional probability distribution of those factors with missing values $[X_{k1}(j), X_{k2}(j), \ldots]$ for the subject j is obtained from
  the known (non-missing) values of factors for subject j and
  the current estimate of the multivariate distribution of all factors.
  F2. Missing values are generated as multivariate Normal deviates from said conditional probability distribution.

Note that the conditional probability distribution automatically includes the effects of the available (non-missing) data in imputing the missing values. Random values generated in this way are distributed with the variance associated with the appropriate conditional probability distributions. In this way, the deviations of imputed values from expected values reflect precisely the uncertainty of imputation based on the statistical model and the known information.

As a utility, e.g., for debugging, the variances can be reduced by any desired factor to check the relationship between uncertainty and objective function. In particular, if said factor is taken as zero, then the method reduces to an EM algorithm.

For the case of a new subject with missing values, the conditional distribution of missing factors given the available factors and the EM solution is obtained as in step C above, and then multiple realizations of the missing values are obtained as Normal deviates as in F2.

Output

The multiple imputed data sets are recorded or piped and thus made available to multiple instances of algorithms for training of a learning-capable system. Using the transformations recorded in the pre-processing step, it is possible to invert any transformations to achieve the desired representation of explanatory variables (e.g., in terms of original laboratory measurements).

The invention has been described for an embodiment in which incomplete (missing) values occur in metric explanatory variables or in ordinal variables that may be treated as if they were metric. The invention provides for an alternative imputation procedure that does not utilize multivariate conditional probability distributions. To estimate the probability of a given explanatory variable, say $x_1$, being missing, a propensity scoring method as described earlier is used, where all the other explanatory variables are included, and only observations in which these remaining variables are not missing are included. Propensity score strata are constructed as above. Within each stratum, the approximate Bayesian bootstrap imputation is applied: Let $n_1$ be the number of subjects for whom $x_1$ is missing out of n subjects in the stratum. A list of $n_1$ observations of $x_1$ is created by drawing randomly with replacement from the $n-n_1$ observed values of $x_1$. An imputed data set is then created by drawing $n_1$ values randomly with replacement from this list and repeating the process sequentially for each stratum and for each variable with missing values. Multiple imputed data sets are created as desired by repeating the approximate Bayesian bootstrap.

The previous imputation procedure using Markov Chain Monte-Carlo iteration is preferred in situations in which the assumption that missing values are correctly modeled by a multivariate conditional probability distribution is appropriate.

Training

Each imputed data set is used to train one or more instances of a learning-capable system as previously described. The results of training are recorded as previously described.

Example

The method of multiple imputation for learning-capable systems is now illustrated by an example. We begin with a simulated "study" of a disease. The probability for the simulated explanatory factors (correlation matrix, variances, and means) is as in Tables 1a and b.

The "true" disease is assumed for the purposes of the example to have an untreated natural median survival of 150 months and is censored at times randomly (uniformly) distributed between 11 and 15 months. The "true" risks were generated according to the nonlinear risk model of Table 7. A baseline hazard is automatically computed to fulfil the specification of median survival. The survival times were generated as earlier using exponential deviates taking the hazard into account.

TABLE 7

Simulated Hazards

| factor | name | log hazard |
|---|---|---|
| 1 | xlypo | 2.00 |
| 2 | xer | 1.00 |
| 3 | xpr | 1.00 |
| 4 | xage | −1.00 |
| 5 | xtum | 1.00 |
| 6 | xupa | 4.00 |
| 7 | xpai1 | 5.00 |
|  | Interaction xupa and xpai1 | −4.00 |

Note that the meaning of the interaction term in the risk may be simply understood from an example: If both factors have the value 1, then the log risk is not 9 as would be generated by the linear model, but rather 5(=4+5−4). If xupa=1 and xpai1=0, then the log risk is 4(=4+0+0).

A total of 5000 simulated subjects were generated according to this risk model.

The coding "missing" was substituted at random for 5% of the 35000 data values (7 factors times 5000 subjects). The number of complete subjects was thus actually only 3510, or about 30% with missing values. These subjects would have been lost to the analysis had listwise deletion been used.

According to the method of the invention, 5 instances of imputed data were generated. For each instance, a neural network was trained to represent the relationship between outcome and explanatory factors. In each case, one-half of the data was randomly chosen for training, the remainder being used as a "generalization" set. Outcome scores were generated for all 5000 subjects from all five neural networks and tabulated. For each patient, the average of the five scores generated from the neural network library and the the variance of these scores were recorded, as well as the "true" risk known from the original data generation procedure.

The square root of the average variance among the five scores for each subject was about 0.5. The square root of the average squared deviation between "true" and estimated risk from the library average was about 1.03. Much of the deviation is in fact attributable to very low or high scores, which one would not expect any system to model accurately because of the censoring at a maximum of 15 months (differences affecting survival between 100 and 150 months are not visible for censoring at 15 months). The average deviation of estimated minus true score in this group was −0.13.

Considering subjects with true scores between −2.0 and +2.0, we find that the square root of the average variance among the five scores for each subject remains virtually unchanged, while the square root of the average squared deviation between "true" and estimated risk from the library average is reduced to about 0.58. Since subjects with very high or low scores are easily classified according to survival anyway, the characteristic on this group is a measure of uncertainty that would be of interest in a decision support type of application. The average deviation of estimated minus true score in this group was −0.07.

Because of exponential statistics, even knowing the "true" risk does not guarantee a correct prediction of outcome, as is well known. As an illustration of quality, we compare the area under the receiver operating characteristic curve (AUC) with respect to the binary variable "relapse" based on "true" and "inferred" risk. The AUC for the true risk is 0.906 (0.895-0.917), whereas for the average inferred risk it is 0.891 (0.88-0.903). This difference translates into a sensitivity difference of 1.2% (83.4 vs. 82.2) at a common specificity level of 80%.

For comparison, 5 neural nets were also trained with the original complete data (2500 training, 2500 generalization each). The square root of the average variance among these five scores for each subject was about 0.27. This compares to about 0.5 for the variance among the 5 neural nets trained by multiple imputation. Using 0.27 as a rough estimate of the variance attributable to training multiple neural networks, roughly one-fourth of the variance of the multiple imputations is associated with the randomness in neural network training, and roughly three-fourths is associated with randomness of multiple imputation. The correlation between the mean of the 5 imputed scores and the mean of the 5 complete data scores is very high, about 0.98.

The invention claimed is:

1. A method for training at least one artificial learning-capable system comprising the steps of:
providing a predetermined training data set comprising a predetermined input data set and a predetermined outcome data set corresponding to input data for each of a respective predetermined number of subjects,
observing survival data relating to patient survival of J subjects,
recording covariates denoted $x_g(j)$ at a reference time $t=0$ relating to events that have not occurred for each subject in any order,
recording special covariates denoted $z_p(j)$ relating to treatments received by each subject,
assuming each subject represents a random sample drawn from a large pool of subjects with identical covariates x, z, defining the conditional probability S(t|x,z) for surviving to time t given x, z,
estimating the p-th propensity score $\phi_p$ corresponding to the probability for subject j to have treatment $z_p=1$,
categorizing the propensity scores into a number $N_p$ of categories, designated as strata, and
augmenting the input data set and/or the outcome data set by the propensity scores and/or the stratum categorization, and
training each artificial learning-capable system using the augmented input data set and/or the augmented outcome data set that was augmented according to the augmenting step, through the use of a computing device.

2. The method according to claim 1, wherein the training step comprises
optimizing operating point parameters within each stratum,
determining the operating point corrections $OP_{kl}(\phi_1, \phi_2, \ldots, \phi_P)$ for shifting the output of the learning capable system $NN_{kl}(X)$ with $X=\{x,z\}$, provided by the learning capable system, given the propensity scores $\phi_1, \phi_2, \ldots, \phi_P$, considering a hazard model $\lambda_k(t|X)=\lambda_{k0}(t)h_k(t|X, \phi_1, \phi_2, \ldots, \phi_P)$,
where k denotes the k-th outcome and the hazard is decomposed as $$h_k(t|X, \phi_1, \phi_2, \ldots, \phi_P) = \exp[\Sigma_{l=1}^L B_l(t)(NN_{kl}(X) - OP_{kl}(\phi_1, \phi_2, \ldots, \phi_P))],$$

wherein $B_l(t)$ are suitable functions comprising the time dependence.

3. The method according to claim 2, wherein the operating point parameters are optimized such that the median of all output data of users assigned to each stratum vanishes.

4. The method according to claim 1, wherein the augmenting step comprises the step of:
generating a plurality of augmented training data sets by augmenting the input data set using a predetermined statistical model.

5. The method according to claim 4, wherein the training step comprises the steps of:
training each of at least two said artificial learning-capable systems using a subset of the plurality of augmented training data sets,
constructing scores for each outcome for each said trained artificial learning-capable system, and
determining characteristics of distributions of the scores for each subject.

6. The method according to claim 5, wherein the input data set is augmented using a generalized Markov chain Monte-Carlo method.

7. The method according to claim 1, wherein the augmenting step comprises the steps of:
providing a further artificial learning capable-system and a further predetermined training data set comprising a further predetermined input data set and a further predetermined outcome data set for each of a respective further predetermined number of subjects,
training the further learning-capable system using the further predetermined training data set, and
augmenting the input data set by at least one additional input variable taken from the further predetermined input data set, further predetermined outcome data set and/or internal output data obtained from the trained further artificial learning-capable system.

8. The method according to claim 7, wherein the additional input variables comprise all further input data and all further outcome data of a subset of subjects of the further training data set.

9. The method according to claim 1, wherein the outcome data of the training data set is time-dependent and the augmenting step comprises pre-transforming a time variable of the training data set in such a way that an associated hazard rate with respect to a predetermined outcome is a predetermined function of the time variable.

10. The method according to claim 1 wherein input data of a subject is applied to the trained artificial learning-capable system to generate an outcome of the artificial learning-capable system, and the method further comprises correcting the outcome with respect to a predetermined reference subject.

11. The method according to claim 6, wherein input data of a subject is applied to at least two artificial learning-capable systems to generate output data of the artificial learning-capable systems, wherein applying input data comprises the steps of:
 presenting the input data of the subject to each of the artificial learning-capable systems and
 constructing a score for the output data obtained from the artificial learning-capable systems.

12. The method according to claim 1, further comprising creating a composite training data set for use in training the artificial learning-capable system, wherein said creating comprises the steps of:
 providing an aggregated evidence data set,
 disaggregating the aggregated evidence data set to obtain a disaggregated training data set based on virtual subjects, and
 merging the disaggregated training data set with a further training data set to produce the predetermined training data set.

13. The method according to claim 12, wherein the merging step comprises the step of choosing a real training data set based on real subjects as the further training data set.

14. The method according to claim 12, wherein the disaggregation step comprises the step of assigning at least a value of one auxiliary variable to each virtual subject of the disaggregated training data set according to predetermined criteria.

15. The method according to claim 1, wherein the predetermined training data set is provided by:
 providing an aggregated evidence data set,
 disaggregating the aggregated evidence data set to obtain a disaggregated training data set based on virtual subjects, and
 merging the disaggregated training data set with a further training data set to produce the predetermined training data set.

16. A computer program product directly loadable into the internal memory of a digital computer, comprising software code portions for performing the steps of the method of claim 1, when said product is run on a computer.

17. A computer program product stored on a medium readable by a computer, comprising computer readable program means for causing a computer to perform the steps of the method of claim 1, when said product is run on a computer.

18. The method according to claim 4, wherein the input data set is augmented using a generalized Markov chain Monte-Carlo method.

19. The method according to claim 13, wherein the disaggregation step comprises the step of assigning at least a value of one auxiliary variable to each virtual subject of the disaggregated training data set.

* * * * *